US008247235B2

(12) United States Patent
Caulfield et al.

(10) Patent No.: US 8,247,235 B2
(45) Date of Patent: Aug. 21, 2012

(54) LIPOPROTEIN ANALYSIS BY DIFFERENTIAL CHARGED-PARTICLE MOBILITY

(75) Inventors: Michael P. Caulfield, Oceanside, CA (US); Richard E. Reitz, San Clemente, CA (US); Shuguang Li, Rancho Santa Margarita, CA (US); Gloria Kwangja Lee, Irvine, CA (US); Ronald Krauss, Berkeley, CA (US); Patricia J. Blanche, Berkeley, CA (US); W. Henry Benner, Danville, CA (US); Earl Cornell, Antioch, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 1204 days.

(21) Appl. No.: 11/760,672

(22) Filed: Jun. 8, 2007

(65) Prior Publication Data

US 2008/0305549 A1 Dec. 11, 2008

(51) Int. Cl.
*G01N 33/92* (2006.01)
*G01N 1/00* (2006.01)
*C07K 1/14* (2006.01)
(52) U.S. Cl. ............ 436/71; 436/63; 436/174; 436/175; 436/177; 530/412; 530/419; 530/427
(58) Field of Classification Search .................... 436/63, 436/71, 174, 175, 177, 178, 536, 538; 435/7.1; 530/412, 419, 427
See application file for complete search history.

(56) References Cited

U.S. PATENT DOCUMENTS

| | | | |
|---|---|---|---|
| 1,825,661 A | 10/1931 | Gull | |
| 4,933,844 A | 6/1990 | Otvos | |
| 5,076,097 A | 12/1991 | Zarrin et al. | |
| 5,247,842 A | 9/1993 | Kaufman et al. | |
| 5,343,389 A | 8/1994 | Otvos | |
| 5,561,515 A | 10/1996 | Hairston et al. | |
| 5,701,012 A | 12/1997 | Ho | |
| 5,756,291 A | 5/1998 | Griffin et al. | |
| 5,788,166 A | 8/1998 | Valaskovic et al. | |
| 5,856,196 A | 1/1999 | Alvarez et al. | |
| 5,895,922 A | 4/1999 | Ho | |
| 5,925,229 A | 7/1999 | Krauss et al. | |
| 5,932,080 A | 8/1999 | Likuski | |
| 5,999,250 A | 12/1999 | Hairston et al. | |
| 6,020,208 A * | 2/2000 | Hutchens et al. | 436/174 |
| 6,145,391 A | 11/2000 | Pui et al. | |
| 6,248,545 B1 | 6/2001 | Kondo et al. | |
| 6,267,579 B1 | 7/2001 | Li et al. | |
| 6,469,297 B1 | 10/2002 | Kato et al. | |
| 6,485,686 B1 | 11/2002 | Wick | |
| 6,491,872 B1 | 12/2002 | Wick | |
| 6,716,994 B1 | 4/2004 | Menchen et al. | |
| 6,753,185 B2 * | 6/2004 | Macfarlane et al. | 436/71 |
| 7,075,066 B2 | 7/2006 | Bailey et al. | |
| 7,259,018 B2 | 8/2007 | Benner et al. | |
| 2002/0098597 A1 | 7/2002 | Koren et al. | |
| 2003/0066969 A1 | 4/2003 | De La Mora | |
| 2003/0136680 A1 | 7/2003 | Benner et al. | |
| 2003/0234356 A1 | 12/2003 | Konermann et al. | |
| 2004/0119009 A1 | 6/2004 | Hanold et al. | |
| 2005/0023455 A1 | 2/2005 | Bailey et al. | |
| 2005/0042695 A1 | 2/2005 | Meares et al. | |
| 2005/0061722 A1 | 3/2005 | Takao et al. | |
| 2007/0048795 A1 | 3/2007 | Fang et al. | |
| 2007/0090026 A1 | 4/2007 | Han et al. | |
| 2008/0302666 A1 | 12/2008 | Benner et al. | |
| 2008/0305549 A1 | 12/2008 | Caulfield et al. | |

FOREIGN PATENT DOCUMENTS

| | | |
|---|---|---|
| EP | 0 546 916 | 6/1993 |
| EP | 1 045 247 | 10/2000 |
| WO | WO-99/17096 | 4/1999 |
| WO | WO-00/51054 | 8/2000 |
| WO | WO-00/65366 | 11/2000 |

OTHER PUBLICATIONS

Atherotech, Inc., Test Benefits—VAP/CAD Lipoprotein Risk Assessment Test, http://home.socal.rr.com/asylem/test_ben.htm, Artherotech, Inc., USA, p. 1-3, 2001.

Bacher et al, Charge-reduced nano electrospray ionization combined with differential mobility analysis of peptides, proteins, glycoproteins, noncovalent protein complexes and viruses, Journal of Mass Spectrometry, 36(9):1038-1052, Sep. 2001.

Barbagallo et al, Influence of ApoE content on receptor binding of large buoyant LDL in subjects with different DLD subclass phenotypes, J. Amer. Heart Association, p. 466-472, 1998.

Bell et al, [LJ.09] The dynamics of a steady Taylor cone electrospray, BAPSDFD98—Abstracts, American Physical Society, USA, Nov. 24, 1998.

Benner et al, Investigating Intact Viruses with Charge-Detection MS and Ion Mobility, Proc. 49th ASMS Conf. on Mass Spectrometry and Allied Topics, ASMS, Chicago IL, May 27, 2001.

Berneis et al., Analysis and quantitation of biotinyfated apoB-containing lipoproteins with streptavidin-Cy3, J. Lipid Res., 43:1155-1159, 2002.

Berneis et al., Metabolic origins and clinical significance of LDL heterogeneity, J. Lipid Res., 43:1363-1379, 2002.

(Continued)

Primary Examiner — Maureen Wallenhorst
(74) Attorney, Agent, or Firm — Foley & Lardner LLP

(57) ABSTRACT

The invention provides methods of preparation of lipoproteins from a biological sample, including HDL, LDL, Lp(a), IDL, and VLDL, for diagnostic purposes utilizing differential charged particle mobility analysis methods. Further provided are methods for analyzing the size distribution of lipoproteins by differential charged particle mobility, which lipoproteins are prepared by methods of the invention. Further provided are methods for assessing lipid-related health risk, cardiovascular condition, risk of cardiovascular disease, and responsiveness to a therapeutic intervention, which methods utilize lipoprotein size distributions determined by methods of the invention.

27 Claims, 9 Drawing Sheets

OTHER PUBLICATIONS

Bundy et al, A novel Method for the Analysis of Complex Biological Protein Mixtures Using Electrospray Ionization Mass Spectrometry Combined with Ion/Ion Chemistry, Proc. 49th ASMS Cont. on Mass Spectrometry and Allied Topics, ASMS, Chicago IL, May 27, 2001.
Campos et al, Predominance of large LDL and reduced HDL2 cholesterol in normolipidemic men with coronary artery disease, Arteriosclerosis, Thrombosis & Vascular Biology, 15(8):1043-1048, Aug. 1995.
Communication dated Jul. 6, 2010 in related EP application 08770383.
Dreon et al, Diet-gene interactions in human lipoprotein metabolism, J. Amer. College of Nutrition, 16(4):313-324,1997.
Dreon et al, LDL subclass patterns and lipoprotein response to a low-fat, high-carbohydrate diet in women, Arteriosclerosis, Thrombosis & Vascular Biology, 17(4):707-714, Apr. 1997.
Dreon et al, Low-density lipoprotein subclass patterns and lipoprotein response to a reduced-fat diet in men, FASEB Journal, 8(1):121-126, Jan. 1994.
Dreon et al, Reduced LDL particle size in children consuming a very-low-fat diet is related to parental LDL-subclass patterns, Am. J. Clin. Nutr., 71:1611-1616, 2000.
Dreon et al., A very low-fat diet is not associated with improved lipoprotein profiles in men with a predominance of large, low-density lipoproteins, Am. J. Clin. Nutr., 69: 411-418, 1999.
Dreon et al., Change in dietary saturated fat intake is correlated with change in mass of large low-density-lipoprotein particles in men, Am. J. Clin. Nutr., 67:828-836, 1998.
Edmonds et al, Capillary Electrophoresis-Electrospray Ionization-Mass Spectrometry, J. Chromatogr., PNL, USA, p. 21-37, 1989.
Feingold et al., The hypertriglyceridemia of acquired immunodeficiency syndrome is associated with an increased prevalence of low density lipoprotein subclass pattern B, Journal of Clinical Endocrinology & Metabolism, 76(6):1423-1427, Jun. 1993.
Gardner et al, Association of small low-density lipoprotein particles with the incidence of coronary artery disease in men and women, Comment in: JAMA, vol. 276(11):875-881, Sep. 18, 1996.
Gray et al, Relation of LDL size to the insulin resistance syndrome and coronary heart disease in American Indians, Arteriosclerosis, Thrombosis & Vascular Biology, 17(11):2713-2720, Nov. 1997.
Haskell et al, Effects of intensive multiple risk factor reduction on coronary atherosclerosis and clinical cardiac events in men and women with coronary artery disease. The Stanford Coronary Risk Intervention Project (SCRIP), Circulation, 89(3):975•990, Mar. 1994.
Havel et al, Genetic underpinnings of LDL size and density: a role for hepatic lipase?, Am. J. Clin. Nutr., 71:1390-1391, 2000.
Henderson et al, Intrinsic Size Parameters for Val, Ile, Leu, Gln, Thr, Phe, and Trp Residues from Ion Mobility Measurements of Polyamino Acid Ions, J. Phys. Chem. B, 103:8780•8785, 1999.
Hodis et al, Intermediate-density lipoproteins and progression of carotid arterial wall intima-media thickness, Circulation, 95(8):2022-2026, Apr. 15, 1997.
International Preliminary Report on Patentability dated Dec. 11, 2009 in related application PCT/US2008/066178.
Jeyarajah et al, Radio signals give new spectrum for cholesterol lipoprotein readings, American Heart Association Journal Report—News Release, American Heart Association, USA, p. 1-3, Jul. 9, 1998.
Katzel et al, Persistence of low HDL-C levels after weight reduction in older men with small LDL particles, Arteriosclerosis, Thrombosis & Vascular Biology, 15(3):299-305, Mar. 1995.
Krauss et al, Detection and quantitation of LDL subfractions, Current Opinion in Lipidology, Current Science Ltd., 3:377-383, 1992.
Krauss et al, Lipoprotein subclasses in genetic studies: the Berkeley data set, Genetic Epidemiology, 10(6):523-528, 1993.
Krauss et al, Low-density-lipoprotein subclasses and response to a low-fat diet in healthy men, American Journal of Clinical Nutrition, 62(2):478S-487S, Aug. 1995.
Krauss et al., Atherogenic lipoprotein phenotype and diet-gene interactions, American Society for Nutritional Science Symposium: Nutritional and Metabolic Diversity: Understanding the Basis of Biologic Variance in the Obesity/Diabetes/Cardiovascular Disease Connection, p. 340S-343S, 2001.
Krauss, R.M., Dietary and genetic effects on low-density lipoprotein heterogeneity, Annu. Rev. Nutr. 21:283-295, 2001.
Krauss, R.M., Is the size of low-density lipoprotein particles related to the risk of coronary heart disease?, JAMA, 287(6): 712-713, Feb. 13, 2002.
Krauss, R.M., Triglyceride-Rich Lipoproteins, LDL Particle Size, and Atherogenesis, American Assoc. of Clinical Endocrinologists Ninth Annual Meeting and Clinical Congress, Amer. Assoc. Clinical Endocrinologists, May 3, 2000.
Legro et al., Alterations in low-density lipoprotein and high-density lipoprotein subclasses among Hispanic women with polycystic ovary syndrome: influence of insulin and genetic factors, Fertility and Sterility, 72(6):990-995, Dec. 1999.
Mack et al, Lipoprotein subclasses in the Monitored Atherosclerosis Regression Study (MARS), Treatment effects and relation to coronary angiographic progression, Arteriosclerosis, Thrombosis & Vascular Biology, 16(5):697-704, 1996.
Muniz et al, A New Tool for the Automated Analysis of LDL Subfraction Patterns Generated by the Lipoprint LDL System, www.4qc.com, Quantimetrix Corporation, USA, p. 1-11, 2001.
New Objective, Inc., Bring Electrospray Into Focus, LC-MS Nano-ESI Proteomics, New Objective, Inc. (www.newobjective.com), USA, 2001.
New Objective, Inc., Product Catalog: Fused Silica Pica Tips, Products (www.newobjective.com), New Objective, Inc., USA, 2001.
New Objective, Inc., What is Electrospray?, Products (www.newobjective.com), New Objective, Inc., USA, 2001.
New Objective, Inc., What New Objective Can Do for You, www.newobjective.com, New Objective, Inc., Cambridge, MA. No date available.
Quantimetrix Corporation, Lipoprint System for LDL Subfraction, Lipoprint Technical—What's New (www.4qc.com), Quantimetrix Corporation, USA, p. 1, 2001.
Stampfer et al, A prospective study of triglyceride level, low-density lipoprotein particle diameter, and risk of myocardial infarction, Comment in: JAMA, 276(11):882-888, Sep. 18, 1996.
Superko et al, Association of lipoprotein subclass distribution with use of selective and non-selective beta-blocker medications in patients with coronary heart disease, Atherosclerosis, 101(1):1-8, Jun. 1993.
Superko et al, Effect of Fluvastatin on Low-density lipoprotein peak particle diameter, Amer. J. of Cardiology, 80:78-81, Jul. 1, 1997.
Superko et al, Garlic powder, effect on plasma lipids, postprandial lipemia, low-density lipoprotein particle size, high-density lipoprotein subclass distribution and lipoprotein(a), J. Am. College of Cardiology, 35(2):321-326, 2000.
Tribble et al., Enhanced oxidative susceptibility and reduced antioxidant content of metabolic precursors of small, dense low-density lipoproteins, Amer. J. of Medicine, 110:103-110, 2001.
TSI Incorporated, Correlation of EM Diameter with Molecular Weight, GEMMA Example—EM Diameter vs. Molecular Weight (www.tsi.com), TSI Incorporated, Particle Instrumentation Division, USA, 1999.
TSI Incorporated, GEMMA Method for Macromolecule/Nanoparticle Analysis, GEMMA Method Product Page (www.tsi.com), TSI Incorporated, Particle Instrument Division, USA, 1999.
TSI Incorporated, Model 3080-Series Electrostatic Clasifiers, TSI Product Info. Sheets (www.tsi.com),TSI Incorporated, USA, 1999.
TSI Incorporated, Model 3312 Ultraviolet Aerodynamic Particle Sizer Spectrometer, Preliminary Product Information (www.tsi.com), TSI Incorporated, USA, 1997.
TSI Incorporated, Model 3313 Fluorescence Aerodynamic Particle Sizer Sensor, 2002, 4 pgs.
TSI Incorporated, Model 3480 Electrospray Aerosol Generator, 3480 Advance Product Information (www. tsi.com), TSI Incorporated, Particle Instrument Division, USA, 1999.
TSI Incorporated, Model 3980 GEMMA Macromolecule Analyzer; TSI Advance Product Information (www.tsi.com), TSI Incorporated, USA, 2000.
TSI Incorporated, Protein Mixture, GEMMA Example—Protein Mixture (www.tsi.com), TSI Incorporated, Particle Instrument Division, USA, 1999.
US Office Action dated May 19, 2010 in related U.S. Appl. No. 11/760,700.

US Office Action dated Sep. 1, 2009 in related U.S. Appl. No. 11/760,700.
Williams et al, Associations of age, adiposity, alcohol intake, menstrual status, and estrogen therapy with high-density lipoprotein subclasses, Arteriosclerosis and Thrombosis, 13(11):1654-1661, Nov. 1993.
Williams et al, Effects of dietary fat on high-density-lipoprotein subclasses are influenced by both apolipoprotein E isoforms and low-density-lipoprotein subclass patterns, American Journal of Clinical Nutrition, 61(6):1234-1240, Jun. 1995.
Williams et al, The associations of high-density lipoprotein subclasses with insulin and glucose levels, physical activity, resting heart rate, and regional adiposity in men with coronary artery disease . . . , Metabolism: Clinical & Experimental, 44(1):106-114, Jan. 1995.
Williams et al, Variability of plasma HDL subclass concentrations in men and women over time, Arteriosclerosis, Thrombosis & Vascular Biology, 17(4):702-706, Apr. 1997.
Williams et al., Low-fat diets, lipoprotein subclasses, and heat disease risk, Am. J. Clin. Nutr., 70:949-950, 1999.
Yang et al., Multilectin affinity chromatography for characterization of multiple glycoprotein biomarker candidates in serum from breast cancer patients. Clinical Chemistry, 52(10): p. 1-9, 2006.
Waugh and Small, Rapid methpod for determining cholesteryl ester transitions of apoB-containing lipoproteins. Journal of Lipid Research, 23:201-204, 1982.
Sigma, R2882 Reactive Green 19-Agarose, Saline suspension, 2007.
Roche, Quick spin protein columns: G-25 sephadex (fine) columns for protein desalting and buffer exchange, Version Jan. 2, 2002.
International Search Report for PCT Patent Application No. PCT/US08/66178, Aug. 20, 2008.
Altintas, et al, Efficient removal of albumin from human serum by monosize dye-affinity beads, (2006), J Chromatography B, 832(2):216-223.
Amthauer, et al, Interaction of cibacron blue and anilinonaphthalenesulphonate with lipoproteins provides a new mean for simple isolation of these plasma proteins, (1988), Biochem Biophys Res Comm, 154(2):752-757.
Axis-Shield PoC AS: Optiprep—product description, (2003), XP002598992, retrieved from URL:http://www.freewebs.com/eldril123/packageinsert/optiprep.pdf, retrieved on Aug. 31, 2010.
Caulfield, et al, Direct determination of lipoprotein particle sizes and concentrations by ion mobility analysis, (2008), Clin Chem, 54(8):1307-1316.
Davies, et al., Rapid separation of LDL subclasses by iodixanol gradient ultracentrifugation, (2003), Clin Chem, 49(11):1865-1872.
Extended European Search Report dated Sep. 20, 2010 in EP application 08770383.
Gardner, et al, Separation of bovine plasma lipoproteins by a rapid ultracentrifugation method, (2003), J Comp Path, 128(1):15-23.
Graham, et al., A novel method for the rapid separation of plasma lipoproteins using self-generating gradient of iodixanol, (1996), Atherosclerosis, 124(1):125-135.
Griffin, et al, Rapid isolation of low density liporpotein LDL subfractions from plasma by density gradient ultracentrifugation, (1990), Atherosclerosis, 83(1):59-68.
Hallberg, et al., Lipoprotein fractionation in deuterium oxide gradients, (1994), J Lipid Research, 35(1):1-9.
US Office Action dated on Oct. 8, 2010 in U.S. Appl. No. 11/760,700.
US Office Action dated Apr. 29, 2011 in U.S. Appl. No. 12/537,191.
Friedewald et al., "Estimation of the Concentration of Low-Density Lipoprotein Cholesterol in Plasma, Without Use of the Preparative Ultracentrifuge", Clinical Chemistry, 18(6) 499-502, 1972.
Jeyarajah et al., "Lipoprotein Particle Analysis by Nuclear Magnetic Resonance Spectroscopy", Clin Lab Med, 26: 847-870, 2006.
Kulkarni et al., "Quantification of cholesterol in all lipoprotein classes by the VAP-II method", Journal of Lipid Research, 35: 159-168, 1994.
Lindgren et al., "Blood Lipids and Lipoproteins: Quantitation, Composition, and Metabolism", Ed. G. L. Nelson, Wiley, p. 181-274, 1992.
Communication pursuant to Article 94(3) EPC dated Apr. 11, 2012 in EP application 08770383.1.

* cited by examiner

LIPOPROTEIN ANALYSIS BY DIFFERENTIAL CHARGED-PARTICLE MOBILITY

FIELD OF THE INVENTION

The present invention generally relates to the fields of particle size analysis and analyses of biological particles including lipoproteins for diagnostic purposes utilizing ion mobility measurement devices and methods. The present invention further provides methods for purification and isolation of biomolecules including, without limitation, lipoproteins and biological complexes containing lipoproteins.

BACKGROUND OF THE INVENTION

The following description is provided solely to assist the understanding of the present invention. None of the references cited or information provided is admitted to be prior art to the present invention. All patents and other references cited in the specification are incorporated by reference in their entireties, including any tables and figures, to the same extent as if each reference had been incorporated by reference in its entirety individually.

Cardiovascular disease is the leading cause of death in the United States. The most commonly used and accepted methods for determining risk of future heart disease include determining serum levels of cholesterol and lipoproteins, in addition to patient demographics and current health. The terms "lipoprotein" and "lipoprotein particle" as well known in the art refer to particles obtained from mammalian blood which include apolipoproteins biologically assembled with noncovalent bonds to package for example, without limitation, cholesterol and other lipids. Lipoproteins preferably refer to biological particles having a size range of 7 to 120 nm, and include VLDL (very low density lipoproteins), IDL (intermediate density lipoproteins), LDL (low density lipoproteins), Lp(a) [lipoprotein (a)], HDL (high density lipoproteins) and chylomicrons as defined herein. "Biological particle" refers to a material having a non-covalently bound assembly of molecules derived from a living source. Examples without limitation of biological particles are lipoproteins assembled for example from apolipoproteins and lipids; viral components assembled from non-covalently bound coat proteins and glycoproteins; immune complexes assembled from antibodies and their cognate antigens, and the like. Lipoprotein density can be determined directly by a variety of physical biochemical methods well known in the art, including without limitation equilibrium density ultracentrifugation and analytic ultracentrifugation. Lipoprotein density may also be determined indirectly based on particle size and a known relationship between particle size and density. Lipoprotein size may be determined by a variety of biochemical methods well known in the art including, without limitation, methods described herein. The term "apolipoprotein" refers to lipid-binding proteins which constitute lipoproteins. Apoliproteins are classified in five major classes: Apo A, Apo B, Apo C, Apo D, and Apo E, as known in the art. There are well established recommendations for cut-off values for biochemical markers, for example without limitation cholesterol and lipoprotein levels, for determining risk. The terms "marker," "biochemical marker" and like terms refer to naturally occurring biomolecules (or derivatives thereof) with known correlations to a disease or condition. However, cholesterol and lipoprotein measurements are clearly not the whole story because as many as 50% of people who are at risk for premature heart disease are currently not encompassed by the ATP III guidelines (i.e., Adult Treatment Panel III guidelines issued by the National Cholesterol Education Program and the National Heart, Lung and Blood Institute).

Methods to measure lipoprotein and other lipids in the blood include, for example without limitation, evaluation of fasting total cholesterol, triglyceride, HDL (high density lipoprotein) and/or LDL (low density lipoprotein) cholesterol concentrations. Currently, the most widely used method for measuring LDL cholesterol is the indirect Friedewald method (Friedewald, et al., *Clin. Chem.*, 1972, 18:499-502). The Friedewald assay method requires three steps: 1) determination of plasma triglyceride (TG) and total cholesterol (TC), 2) precipitation of VLDL(very low density lipoprotein) and LDL, and 3) quantitation of HDL cholesterol (HDLC). Using an estimate for VLDLC as one-fifth of plasma triglycerides, the LDL cholesterol concentration (LDLC) is calculated by the formula: LDLC=TC−(HDLC+VLDLC). While generally useful, the Friedewald method is of limited accuracy in certain cases. For example, errors can occur in any of the three steps, in part because this method requires that different procedures be used in each step. Furthermore, the Friedewald method is to a degree indirect, as it presumes that VLDLC concentration is one-fifth that of plasma triglycerides. Accordingly, when the VLDL of some patients deviates from this ratio, further inaccuracies occur.

Another method for evaluating blood lipoproteins contemplates measurement of lipoprotein size and density. The size distribution of lipoproteins varies among individuals due to both genetic and nongenetic influences. The diameters of lipoproteins typically range from about 7 nm to about 120 nm. The term "about" in the context of a numerical value represents the value +/−10% thereof. In this diameter size range, there exist subfractions of the particles that are important predictors of cardiovascular disease. For example, VLDL transports triglycerides in the blood stream; thus, high VLDL levels in the blood stream are indicative of hypertriglyceremia. These subfractions can be identified by analytical techniques that display the quantity of material as a function of lipoprotein size or density.

Regarding lipoprotein density analysis, ultracentrifugally isolated lipoproteins can be analyzed for flotation properties by analytic ultracentrifugation in different salt density backgrounds, allowing for the determination of hydrated LDL density, as shown in Lindgren, et al, *Blood Lipids and Lipoproteins: Quantitation Composition and Metabolism*, Ed. G. L. Nelson, Wiley, 1992, p. 181-274, which is incorporated herein by reference. For example, the LDL class can be further divided into seven subclasses (see Table 1) based on density or diameter by using a preparative separation technique known as equilibrium density gradient ultracentrifugation. It is known that elevated levels of specific LDL subclasses, LDL-IIIa, IIIb, IVa and IVb, correlates closely with increased risk for CHD (i.e., coronary heart disease), including atherosclerosis. Furthermore, determination of the total serum cholesterol level and the levels of cholesterol in the LDL and HDL fractions are routinely used as diagnostic tests for coronary heart disease risk. Lipoprotein class and subclass distribution is a more predictive test, however, since it is expensive and time-consuming, it is typically ordered by physicians only for a limited number of patients.

With respect to measurement of the sizes of lipoproteins, currently there is no single accepted method. Known methods for measuring the sizes of lipoproteins within a clinical setting include the vertical auto profile (VAP) (see e.g. Kulkarni, et al., *J. Lip. Res.*, 1994, 35:159-168) whereby a flow analyzer is used for the enzymatic analysis of cholesterol in lipoprotein classes separated by a short spin single vertical ultracentrifugation, with subsequent spectrophotometry and analysis of the resulting data. Another method (see e.g. Jeyarajah, E. J. et al., *Clin Lab Med.*, 2006, 26:847-70) employs nuclear magnetic resonance (NMR) for determining the concentrations of lipoprotein subclasses. In this method, the NMR chemical shift spectrum of a blood plasma or serum sample is obtained. The observed spectrum of the entire plasma sample is then matched by computer means with known weighted sums of previously obtained NMR spectra of lipoprotein subclasses. The weight factors that give the best fit between the sample spectrum and the calculated spectrum are then used to estimate the concentrations of constituent lipoprotein subclasses in the blood sample. Another method, electrophoretic gradient gel separation (see e.g. U.S. Pat. No. 5,925,229 incorporated by reference herein) is a gradient gel electrophoresis procedure for the separation of LDL subclasses. The LDL fractions are separated by gradient gel electrophoresis, producing results that are comparable to those obtained by ultracentrifugation. This method generates a fine resolution of LDL subclasses, and is used principally by research laboratories. However, the gel separation method, which depends on uniform staining of all components that are subsequently optically measured, suffers from nonuniform chromogenicity. That is, not all lipoproteins stain equally well. Accordingly, the differential stain uptake can produce erroneous quantitative results. Additionally, the nonuniform chromogenicity can result in erroneous qualitative results, in that measured peaks may be skewed to a sufficient degree as to cause confusion of one class or subclass of lipoprotein with another. Furthermore, gradient gel electrophoresis can take many hours to complete. It would be useful if gradient gel electrophoresis separation times could be shortened and the analysis simplified so that high resolution lipid analysis could be used in clinical laboratories as part of a routine screening of blood samples, and for example to assign a risk factor for cardiovascular disease.

Accordingly, a high-resolution methodology for measuring all subclasses of LDL as well as VLDL, IDL (intermediate density lipoprotein), HDL, Lp(a) and chylomicron particles that is accurate, direct, and complete, would be an important innovation in lipid, including lipoprotein, measurement technology. If inexpensive and convenient, such an assay could be employed not only in research laboratories, but also in a clinical laboratory setting. Ideally, clinicians could use this information to improve current estimation of coronary disease risk and make appropriate medical risk management decisions based on the assay.

Indeed, more recent methods for the quantitative and qualitative determination of lipoproteins from a biological sample have been described by Benner et al (U.S. Pub. App. No. 2003/0136680, filed Nov. 12, 2002, and incorporated by reference in its entirety herein) which methods employ particulate size and/or ion mobility devices.

Ion mobility, also known as ion electrical mobility or charged-particle mobility, analysis offers an advantage over the other methods described herein in that it not only measures the particle size accurately based on physical principles but also directly counts the number of particles present at each size, thereby offering a direct measurement of lipoprotein size and concentration for each lipoprotein. Ion mobility analysis has been used routinely in analyzing particles in aerosols, and analyzers suitable for ion mobility analysis have been adapted to analyze large biological macromolecules. See e.g. Benner et al. (Id.) Ion mobility analysis is a very sensitive and accurate methodology with, nonetheless, a drawback that ion mobility analysis measures all particles introduced into the system. Accordingly, it is of prime importance to isolate and/or purify the compounds of interest prior to analysis. Lipoproteins are candidates for this method because lipoproteins can be isolated from other serum proteins based on density and other features described herein. Accordingly, by the present invention there are provided methods for purification and isolation of biomolecules including, without limitation, lipoproteins and biological complexes containing lipoproteins, for use in ion mobility analysis. The present invention further provides apparatus and methods for conducting ion mobility analyses.

SUMMARY OF THE INVENTION

By the present invention there are provided methods for the preparation of sample for, and apparatus useful for, differential charged-particle mobility analysis (also referred to herein as "ion mobility analysis") of lipoproteins utilizing a gas-phase electrophoretic-mobility molecular analyzer.

In a first aspect the invention provides a method for purifying lipoproteins suitable for ion mobility analysis of lipoprotein class and subclass, which method includes the following steps: (a) preparing a centrifuge tube containing a first solution underneath a sample, which sample comprises one or more lipoproteins and non-lipoprotein components, which first solution has a first density greater than 1.00 g/mL and less than or equal to about 121 g/mL; and (b) subjecting the tube to contrifugation sufficient to cause the non-lipoprotein components to migrate toward the bottom of the tube and away from the lipoproteins, thereby providing purified lipoproteins. In some embodiments, the first density is in the range of about 1.15 g/mL to about 1.21 g/mL.

In the context of this aspect of the invention, the sample containing lipoproteins is obtained by processing of a blood specimen from a mammal as described herein, which processing optionally includes adjustment of density by the addition of salts including for example, without limitation, the Cl, Br, and/or I salts of Na, K, and/or Cs.

"Centrifugation" means separation or analysis of substances in a solution as a function of density and density-related molecular weight by subjecting the solution to a centrifugal force generated by high-speed rotation in an appropriate instrument.

As used herein, "purify" and like terms refer to an increase in the relative concentration of a specified component with respect to other components. For example without limitation, removal of lipid from a lipoprotein solution constitutes purification of the lipoprotein fraction, at e.g. the expense of the lipid fraction. It is understood that "purifying" and like terms in the context of centrifugation refers to sufficient separation in a centrifuge tube following centrifugation to allow extraction of the separated components by methods well known in the art including, without limitation, aspiration and/or fractionation. Surprisingly, it has been found that reducing the density of lipoprotein-containing solutions prior to centrifugation for example, without limitation, by reducing the salt concentration thereof, results in enhanced recovery of certain fractions of lipoprotein, including LDL and HDL fractions.

Further to this aspect of the invention are provided in certain embodiments a second solution within the centrifuge tube, above and adjacent to the sample, which second solution is preferably an aqueous solution, more preferably water or deuterated forms thereof, of lower density than the first solution. Accordingly, the density of the second solution is greater than or equal to 1.00 g/mL and less than the density of the first solution. Surprisingly, it has been found that overlaying a lipoprotein-containing sample in a centrifuge tube with a solution having lower density results in enhanced recovery of lipoprotein following centrifugal separation. Without wishing to be bound by any theory, it is believed that ionic flow from the more dense lipoprotein-containing solution to the less dense, preferably aqueous, overlaid second solution modulates the buoyancy of lipids therein, resulting in enhanced recovery of lipoprotein.

In another aspect, the invention provides yet a further method for purifying lipoproteins, which method includes the following steps: (a) preparing a centrifuge tube containing a sample and a first solution located below and adjacent the sample, the sample comprising one or more lipoproteins and non-lipoprotein components, the sample further comprising Reactive Green dextran and dextran sulfate (DS), the first solution comprising deuterium oxide ($D_2O$); and (b) subjecting the centrifuge tube to centrifugation sufficient to cause the non-lipoprotein components to migrate toward the bottom of the tube and away from the lipoproteins. In some embodiments, the purified liporoteins so separated are then removed for ion mobility analysis. In some embodiments, the density of the first solution is in the range 1.1 g/mL to about 1.21 g/mL. In some embodiments, the density of the first solution is in the range 1.00 g/mL to about 1.10 g/mL. In some embodiments, the first solution comprises $D_2O$. In some embodiments, the first solution is substantially $D_2O$.

In another aspect, the invention provides methods for purifying lipoproteins for ion mobility analysis, which methods do not include centrifugation, which methods include the following steps: a) admixing a solution comprising lipoproteins and non-lipoproteins with one or more polyanionic compounds and one or more divalent cations; b) allowing a precipitate containing lipoproteins to form in the admixed solution; and c) after step b), collecting the precipitated lipoproteins and subjecting the precipitated lipoproteins to ion mobility analysis after resolubilization.

In another aspect, the invention provides methods for purifying lipoproteins for ion mobility analysis, which methods do not include centrifugation, which methods include the following steps: a) admixing a solution comprising lipoproteins and non-lipoproteins with one or more lipoprotein-capture ligands capable of binding lipoproteins to form a lipoprotein/lipoprotein-capture ligand complex; b) isolating the lipoprotein/lipoprotein-capture ligand complex; and c) releasing the lipoproteins from the lipoprotein/lipoprotein-capture ligand complex and subjecting the lipoproteins to ion mobility. In some embodiments, the lipoproteins are selected from the group consisting of HDL, LDL, Lp(a), IDL and VLDL. In some embodiments, the lipoprotein-capture ligand is selected from the group consisting of aptamer and antibody. In some embodiments, the lipoprotein-capture ligand is an antibody.

Further any of the aspects contemplating isolation and/or purifying of lipoproteins described herein, in another aspect the invention provides methods for analyzing the size distribution of lipoproteins, which method includes the following steps: (a) providing one or more lipoproteins in accordance with any of the methods described herein; and (b) subjecting the one or more lipoproteins to ion mobility analysis, thereby determining the size distribution of the lipoproteins. In a further embodiment, this method is used to determine in a patient sample the concentration of HDL, LDL, IDL, and VLDL and more preferably HDL, LDL, IDL, VLDL and Lp(a). The patient sample is preferably plasma or serum. The method may also include use of an internal standard such as one or more labeled lipoproteins (e.g. fluorescent label) to monitor sample loss during processing so as to obtain more accurate determinations of lipoprotein concentration in the starting sample to be evaluated.

In another aspect of the invention, an apparatus for differential mobility analysis comprises one or more pumps adapted to transport sample through a capillary, an ionizer adapted to charge particles of the sample as the sample flows within the capillary, and an ion mobility analyzer adapted to perform a differential mobility analysis on the sample of charged particles. The ionizer may include a conductive union around a part of the capillary. In one embodiment, the conductive union forms a microtite region in a part of the capillary and applies a charge to the sample flowing therethrough, thereby charging particles of the sample.

Certain embodiments of the apparatus further comprise an autosampler adapted to provide a sample for differential mobility analysis to the one or more pumps.

In some embodiments, the one or more pumps include a high-flow pump adapted to provide the sample to a nanoflow pump, the nanoflow pump being adapted to provide the sample to the capillary. The high-flow pump may pump sample at a rate of approximately 15-25 microliters per minute, and the nanoflow pump may pump the sample at a rate of approximately 100-200 nanoliters per minute.

Figure 6:
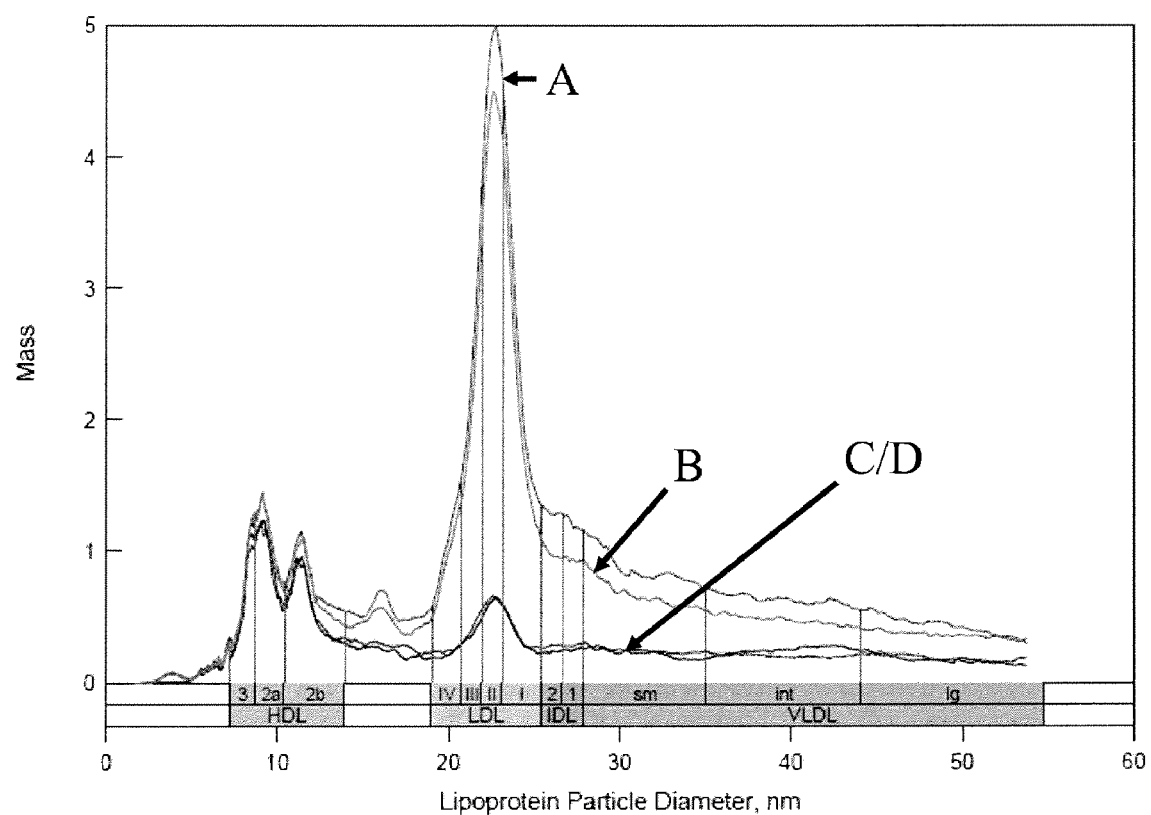

FIG. 6 shows the result of inclusion of DS in the dilution buffer following traditional density separation and dialysis. A and B: 5 ug/mL DS included in the ammonium acetate dilution buffer. C and D: no DS in the ammonium acetate dilution buffer. The abscissa is lipoprotein diameter (nm), and the ordinate is an arbitrarily scaled mass coordinate, as discussed in the legend for FIG. 1.

Figure 7:
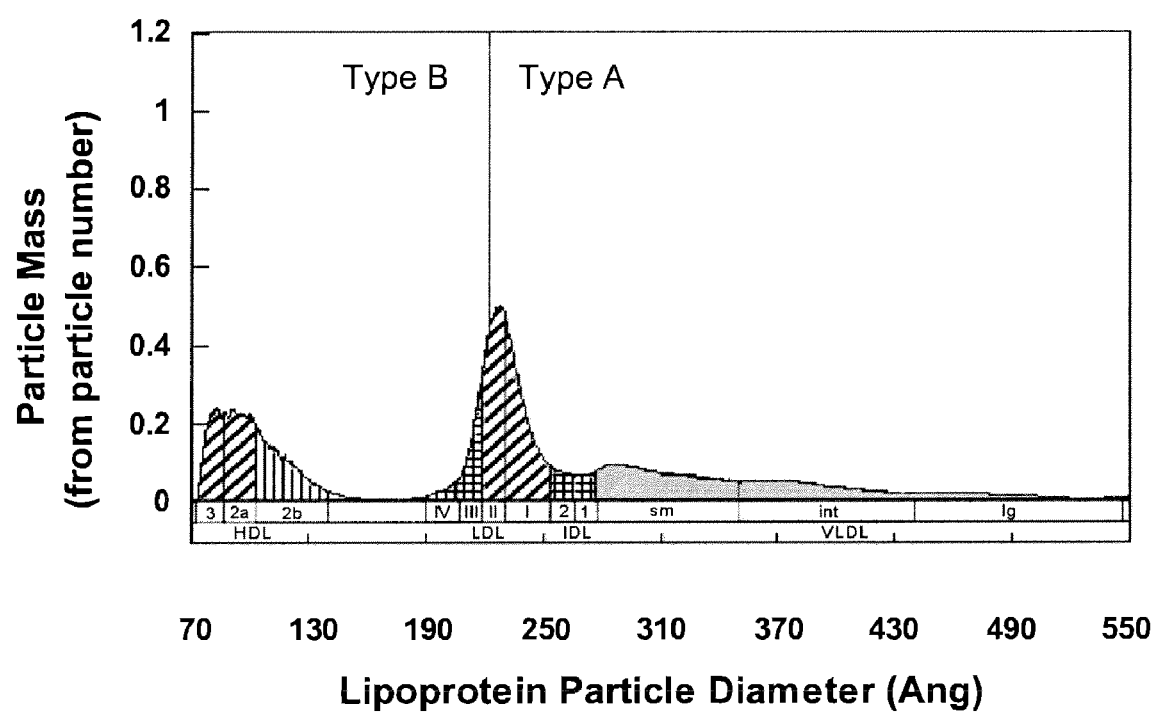

FIG. 7 shows the resulting lipoprotein profile in conjunction with a typical report on lipoprotein fractionation by ion mobility. The abscissa is lipoprotein diameter (nm), and the ordinate is a mass, calculated from ion mobility data and parameters as known in the art. Areas shown with cross-hatching indicate relative risk, with the diagonal-lined sections representing medium risk, vertical-lined sections representing lower risk, cross-hatched sections representing higher risk, and the shaded sections representing indeterminate risk.

Figure 8:
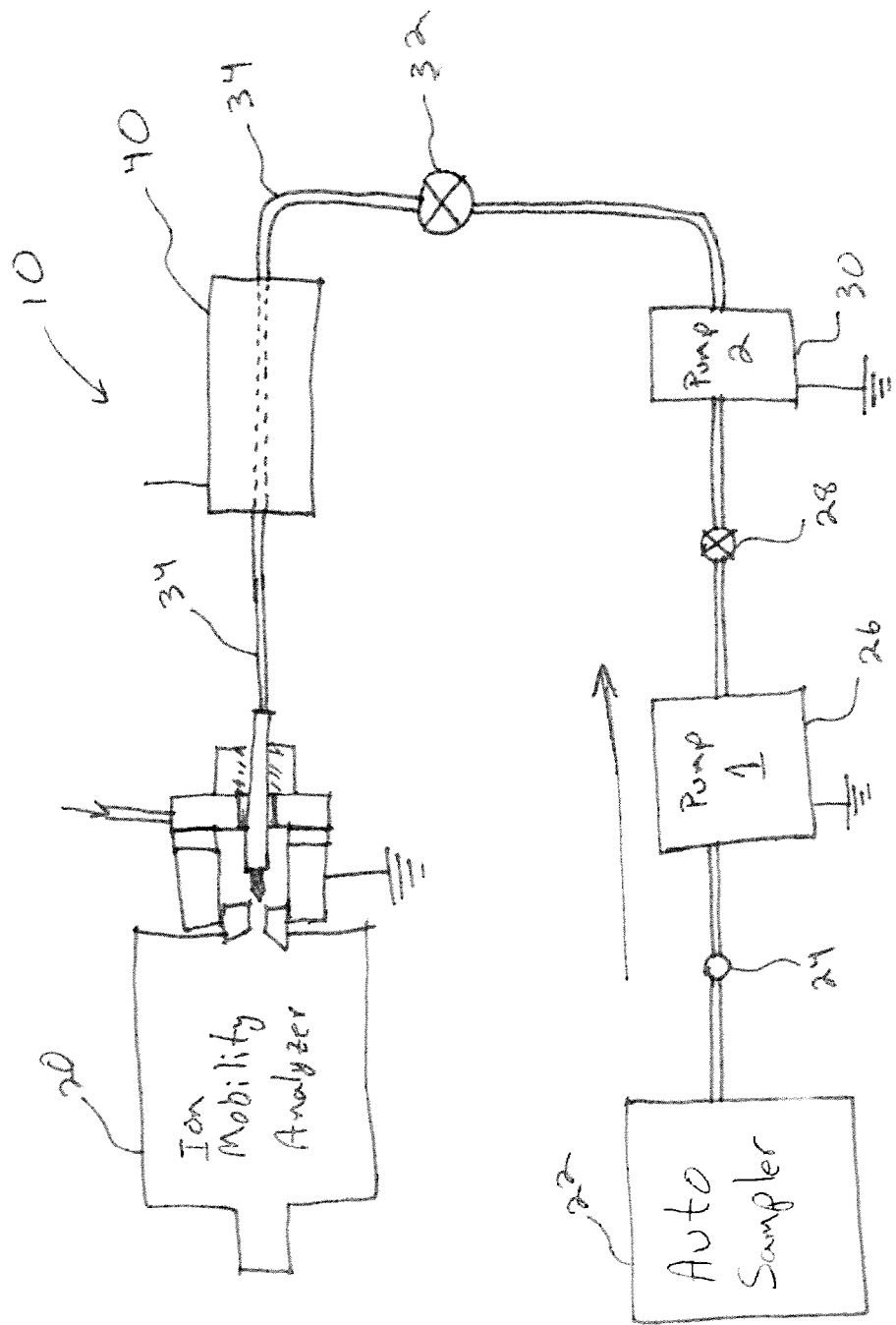

FIG. 8 illustrates an apparatus for ion mobility analysis according to an embodiment of the present invention.

Figure 9B:
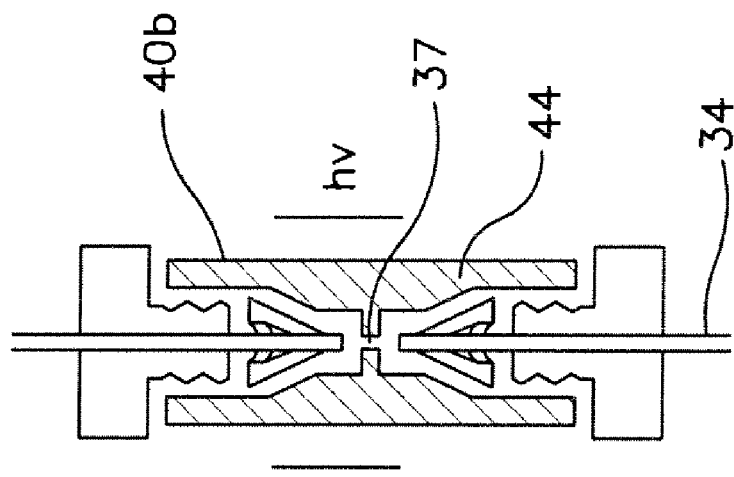
Figure 9A:
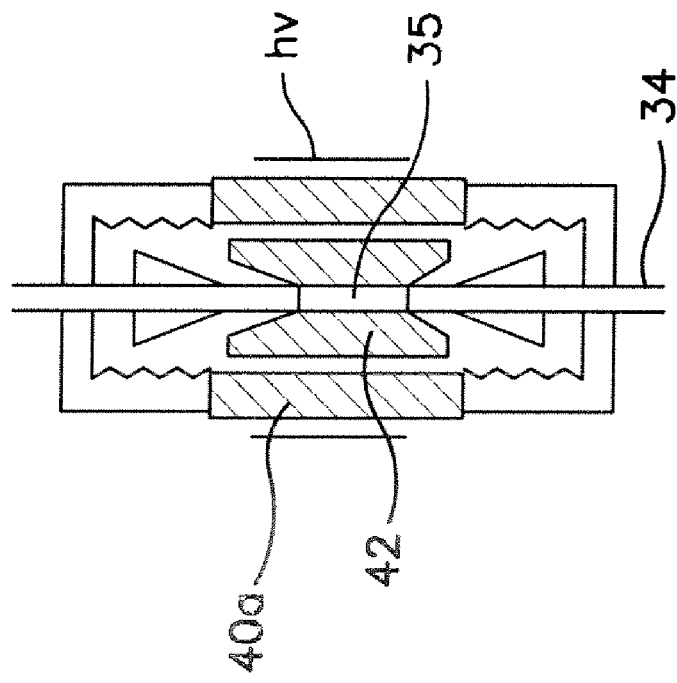

FIGS. 9A and 9B illustrate embodiments of conjunctive unions for use with the apparatus of FIG. 8.

DETAILED DESCRIPTION OF THE INVENTION

"VLDL, IDL, LDL, and HDL" refer to classifications of lipoproteins as shown in Table 1. It is understood that the values used in Table 1 for sizes are determined by gel electrophoresis methods, as known in the art. With the ion mobility analysis methods disclosed here, it has been observed that all measurements of lipoprotein diameter obtained with ion mobility analysis are shifted to smaller diameters compared to the data obtained with gel electrophoresis. Without wishing to be bound by any theory, it is believed that this difference is due to calibration of the gels. The shift appears to be linearly related and approximated by the following formula:

$$0.86 * \text{gel diameter} = IM \text{ diameter}$$

Table 1 describes the standard classes and subclass designations assigned to various lipoprotein fractions using traditional gel electrophoresis measurements: very low density lipoproteins (VLDLs) with subclasses VLDL I and II; intermediate density lipoproteins (IDLs) with subclasses IDL I and II,; low density lipoproteins (LDLs) with subclasses I, IIa, IIb, IIIa, IIIb, IVa and IVb; and high density lipoproteins (HDLs), which typically includes several subclasses, such as HDL IIa, IIb, IIIa, IIIb, and IIIc.

TABLE 1

Major Lipoprotein Class, Subclass, Density and Particle Size

| Class Acronym Subclass | Name Density (g/mL) | Particle Diameter (Å) |
|---|---|---|
| VLDL | Very Low Density Lipoprotein | |
| I | <1.006 | 330-370 |
| II | 1.006-1.010 | 300-330 |
| IDL | Intermediate Density Lipoprotein | |
| I | 1.006-1.022 | 285-300 |
| II | 1.013-1.019 | 272-285 |

TABLE 1-continued

Major Lipoprotein Class, Subclass, Density and Particle Size

| Class Acronym Subclass | Name Density (g/mL) | Particle Diameter (Å) |
|---|---|---|
| LDL | Low Density Lipoprotein | |
| I | 1.019-1.023 | 272-285 |
| IIa | 1.023-1.028 | 265-272 |
| IIb | 1.028-1.034 | 256-265 |
| IIIa | 1.034-1.041 | 247-256 |
| IIIb | 1.041-1.044 | 242-247 |
| IVa | 1.044-1.051 | 233-242 |
| IVb | 1.051-1.063 | 220-233 |
| HDL | High Density Lipoprotein | |
| IIa | 1.063-1.100 | 98-130 |
| IIb | 1.100-1.125 | 88-98 |
| IIIa | 1.125-1.147 | 82-88 |
| IIIb | 1.147-1.154 | 77-82 |
| IIIc | 1.154-1.203 | 72-77 |

Without wishing to be bound by any theory, it is believed that the observed differences between ion mobility analysis diameters and gel electrophoresis diameters may also be due to distortion of lipoproteins interacting with the gel matrix under the influence of the intrinsic impressed electric field of the electrophoresis gel. The size difference may also be due to historical data used to convert particle density (obtained from analytic ultracentrifuge separations) to particle size obtained from electron microscopy.

"Chylomicrons" means biological particles of size 70-120 nm, with corresponding densities of less than 1.006 g/mL. Chylomicrons have not been found to have any clinical significance in the prediction of heart disease, for example CHD.

"Apo A" as known in the art is a protein component of HDL. "Apo B" is a protein component of LDL, IDL, Lp(a), and VLDL, and indeed is the primary apolipoprotein of lower density lipoproteins, having human genetic locus 2p24-p23, as known in the art.

"Albumin" refers to ubiquitous proteins constituting approximately 60% of plasma, having density about 1.35 g/mL, as known in the art.

"Lp(a)," and "lipoprotein (a)" refer to a type of lipoprotein found in serum having a molecular composition distinct from IDL and LDL, which is found in complex with apolipoprotein a [apo(a)]. Lp(a) has a particle size that overlaps with LDL and IDL and therefore can interfere with particle size analysis when Lp(a) particles are present in the sample. Although some patients have naturally occurring low Lp(a) concentrations, it is believed to be good practice to remove the Lp(a) prior to LDL size measurements to preclude otherwise inaccurate measurements for those patients having significant Lp(a) concentrations. In this manner, potential Lp(a) size interference problems can be avoided.

The present invention contemplates methods of ion mobility, and preparation of samples for ion mobility analysis. Ion mobility utilizes the principle that particles of a given size and charge state behave in a predictable manner when carried in a laminar-air flow passed through an electric field. Accordingly, ion mobility analysis is a technique to determine the size of a charged particle undergoing analysis when the charged particle is exposed to an electric field.

Electrical mobility is a physical property of an ion and is related to the velocity an ion acquires when it is subjected to an electrical field. Electrical mobility, Z, is defined as $$Z = \frac{V}{E} \quad (1)$$

where V=terminal velocity and E=electrical field causing particle motion. Particle diameter can be obtained from $$Z = \frac{neC_c}{3\pi\eta d} \quad (2)$$

where n=number of charges on the particle (in this case a single charge), $e=1.6.\times0.10^{-19}$ coulombs/charge, $C_c$=particle size dependent slip correction factor, $\eta$=gas viscosity, and d=particle diameter. Accordingly, solving for d, provides the following relationship:

$$d = \frac{neC_c}{3\pi\eta}\frac{E}{V}. \quad (3)$$

Thus, an explicit relationship for particle diameter as a function of known parameters results. By setting the parameters to different values, different particle diameters of the charged particles may be selected as further described below and known in the art. In preferred methods of ion mobility analysis, the electric field strength E acting upon the charged particle is varied during analysis.

In ion mobility analysis, particles (e.g., lipoproteins and the like) are carried through the system using a series of laminar airflows. The lipoproteins in a volatile solution are introduced to an electrospray chamber containing approximately 5% $CO_2$ wherein the lipoproteins desolvate. In the electrospray chamber the desolvated, charged lipoproteins are neutralized by ionized air, introduced for example without limitation by an alpha particle emitter in the chamber. Based on Fuch's formula, a predictable proportion of particles emerge from the chamber carrying a single charge and are transported from the chamber to the Differential Mobility Analyzer (DMA). For details on Fuch's formula, reference is made to Fuchs, N. A.: *The Mechanics of Aerosols*, Macmillan, 1964. "Differential Mobility Analyzer," "DMA" and like terms refer to devices for classifying charged particles on the basis of ion electrical mobility, as known in the art and described herein. In ion mobility analysis, when particles have a known uniform charge, the size of the particles classified may be determined from the mobility thereof. In the DMA the particles enter at the top outer surface of the chamber and are carried in a fast flowing laminar-air flow, (i.e., "the sheath flow"). The sheath flow is filtered (to remove particles) air that constantly recirculates through the DMA at a constant velocity of 20 L/min. As the particles pass through the DMA (carried in the sheath flow) the electric potential across the chamber is ramped up at a known rate. As the electrical potential changes, particles of different diameter are collected via a slit at the bottom inner surface of the chamber. Particles follow a non-linear path through the DMA depending on their charge and diameter. At any given electrical potential, particles of known size will follow a path that will allow them to pass through the collecting slit. Particles passing through the collecting slit are picked up by another, separate laminar-flow air stream and are carried to a particle counter. The particle counter enlarges the particles by condensation to a size that can be detected and counted for example by a laser detection system. Knowing the electrical potential being applied to the DMA when the particle was collected permits the accurate determination of the particle diameter and the number of particles present at that size. This data is collected and stored in bins as a function of time for different particle size. In this way the number of particles of any given size range can be determined and converted to a concentration of particles based on the time required to collect the data, the flow rate of sample being introduced into the electrospray device, and the number of charged particles at that size.

In methods of the present invention contemplating isolation and/or purification of lipoproteins, initial sample collection and preparation may be conducted by methods well known in the art. Typically, a 2 to 5 ml fasting blood specimen is initially taken. Chylomicrons are not typically present in subjects who have been fasting for a period of at least 12 hours; thus, overlap of VLDL sizes and chylomicron sizes is eliminated by fasting. The specimen is then initially spun in a centrifuge (e.g., clinical centrifuge) preferably for approximately 10 minutes at approximately 2000×G, which centrifugation is sufficient to remove the cellular components from the specimen. During this process, the more dense cellular components stratify at the bottom of the sample. A remaining less dense plasma specimen containing lipoproteins on top is then drawn off using methods well known in the art, e.g., aspiration.

Historically, in preparation for centrifugation, a plasma specimen could be density-adjusted to a specific density using high purity solutions or solids of inorganic salts, e.g., sodium chloride (NaCl), sodium bromide (NaBr) and the like. In some previous protocols, the specific density would be chosen to be greater than or equal to the highest density of the lipoprotein material to be analyzed, so that the lipoprotein material would float when density stratified. "Density stratified" and like terms refer to the layering of components in a solution subjected to centrifugation. These densities are tabulated in Table 1, table of lipoprotein classes, subclasses, densities, and sizes. The density-adjusted sample could then be ultracentrifuged for example for approximately 18 hours at 100,000×G to separate the non-lipoprotein proteins from the lipoproteins. Non-lipoprotein proteins, particularly albumin, are removed from the plasma specimen, preferably by this ultracentrifugation step. The lipoproteins float to the top of the sample during ultracentrifugation. Accordingly, by sequentially centrifuging from lowest density to highest density of the density adjustment, the various classes and subclasses of lipoproteins could be sequentially extracted. Typically, a dialysis step would be required following extraction of a centrifuged sample to remove salts introduced for adjustment of density, which dialysis step would typically require 4-12 hrs under conditions well known in the art.

Conditions for centrifugation for lipoprotein-containing samples described herein are well known in the art of biochemical separation. For example without limitation, samples are typically centrifuged at 10 C for 1-4 hrs at 223,000×G. In some embodiments, centrifugation employs centrifugal force of 50,000-100,000, 100,000-120,000, 120,000-150,000, 150,000-200,000, 200,000-230,000, 230,000-250,000×G, or even higher force. In some embodiments, the time of centrifugation is 1, 2, 2.2, 2.4, 2.6, 2.8, 3.0, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18 hr, or even longer. Prior to analysis by ion mobility, an aliquot of the lipid fraction is removed (e.g., 10-200 µL) from the top of the centrifuge tube and diluted (e.g., 1:800) in 25 mM ammonium acetate (AA), 0.5 mM ammonium hydroxide, pH 7.4. Advantageously, in some embodiments described herein, a dialysis step is not necessary in conjunction with methods of the invention, resulting in less time required for analysis.

In embodiments of the invention which contemplate lipoproteins, the lipoproteins are selected from the group consisting of HDL, LDL, IDL, Lp(a), and VLDL. In some embodiments, the lipoproteins are HDL.

In some embodiments of aspects provided herein which contemplate lipoproteins, the lipoproteins may derive from a plasma specimen, obtained by methods well known in the art or as described herein. The terms "biological specimen," "biological sample" and like terms refer to explanted, withdrawn or otherwise collected biological tissue or fluid including, for example without limitation, whole blood, serum and plasma. The term "plasma" in the context of blood refers to the fluid obtained upon separating whole blood into solid and liquid components. The term "serum" in the context of blood refers to the fluid obtained upon separating whole blood into solid and liquid components after it has been allowed to clot. In some embodiments of any of the aspects of the present invention, the biological specimen is of human origin. In some embodiments of any of aspects provided herein, the biological specimen is serum. In some embodiments of any of the aspects provided herein, the biological specimen is plasma.

In some embodiments of the invention which contemplate centrifugation, the centrifugation does not reach equilibrium. "Centrifugation equilibrium" and like terms refers to centrifugation conducted for sufficient time and at sufficient centrifugal force such that the components of the solution being centrifuged have reached neutral density buoyance, as well known in the art. Surprisingly, it has been found that foreshortened centrifugation protocols, as described herein wherein centrifugal equilibrium is not reached, can nonetheless provide significant purification of lipoproteins.

In some embodiments of the invention which contemplate centrifugation of sample containing lipoproteins and non-lipoprotein components, purified lipoprotein is collected from the top portion of the centrifuge tube following centrifugation. "Top portion of the centrifuge tube" and like terms refer to the liquid in the upper portion of a centrifuge tube when viewed outside of the centrifuge rotor which may, but does not necessarily, include liquid at the very top.

Further any of the methods of the present invention directed to purifying lipoproteins, it has been surprisingly found that reduction of the density of the solution to a value less or equal to about 1.21 g/mL while centrifuging to less than equilibrium actually results in improved recovery, hence purification, of LDL and HDL.

Figure 1:
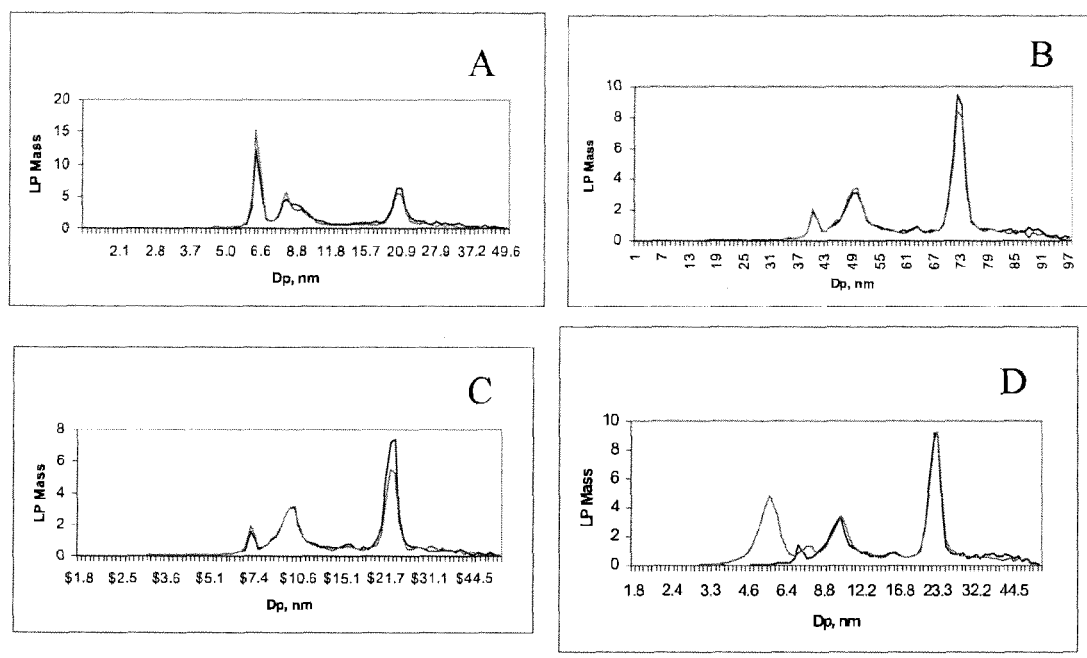
FIG. 1 shows the effect of density on lipoprotein recovery from a plasma sample during a 3.7 hr ultracentrifugation. Samples were prepared in duplicate using different density solutions and centrifugation for 3.7 hr. After collecting the lipoprotein fraction, it was dialyzed before analysis by Ion Mobility. Each panel shows the profile of each replicate. Solution densities: A=1.23 g/mL; B=1.181 g/mL; C=1.170 g/mL; D=1.165 g/mL. The abscissa is lipoprotein diameter (nm) and the ordinate is an arbitrarily scaled mass coordinate, which mass coordinate is linearly related to the actual number of particles counted as a function of size (i.e., diameter).

Exemplary ion mobility results for lipoproteins from plasma samples purified by centrifugation with varying densities of solution are shown in FIG. 1. In these experiments, serum samples (25 uL) were overlaid on a cushion (200 uL) of four different density salt (KBr) solutions. The densities of the solutions were 1.165, 1.170, 1.181, and 1.23 g/mL. Each sample was ultracentrifuged for a period of 3.7 hr at 223,000× G. The top 100 uL after the centrifugation was removed. Fractionated lipoprotein samples from each density were dialyzed overnight against ammonium acetate (25 mM), ammonium hydroxide (0.5 mM), pH 7.4. Following dialysis each sample was analyzed by ion mobility with the resulting profiles shown in FIG. 1. A reduction is apparent in the lipoprotein profiles in the HDL region seen at the lower densities compared to 1.23 g/mL. Without wishing to be bound by any theory, this observation is believed due to more efficient removal of plasma proteins with lower salt solutions.

With further reference to FIG. 1, the abscissa is the particle size (i.e., diameter), and the ordinate is an arbitrarily scaled mass. The area under the curves, in a particle mass versus independent variable (such as size, density, mobility, etc.) distribution, is directly representative of the lipoprotein particle mass. The measurement technique relies on counting individual particles as a function of size (diameter). It is therefore possible to convert the number of particles at a specific size into a mass value using the volume and density of the particles. The density of lipoproteins is a well-known function of particle size and is obtainable for example from the literature. The mass values associated with the figure are simply scaled to indicate relative values but can be converted to actual mass of lipoproteins in plasma using dilution factors along with flow rates of sample and air passing through the ion mobility spectrometer. Accordingly, in some embodiments adjusting the density of a lipoprotein-containing solution prior to non-equilibrium centrifugation to a value lower than expected to separate the higher density lipoproteins (e.g., HDL) actually results in separation of HDL and LDL. Advantageously, the method of reducing the density of the lipoprotein-containing sample also results in increased separation from albumin.

In some embodiments of aspects provided herein contemplating centrifugation of a sample containing lipoproteins and non-lipoprotein components, the first solution comprises $D_2O$. In some embodiments, the density of the first solution is determined substantially by the content of $D_2O$, wherein the first solution has a density in the range 1.00 to about 1.10 g/mL. The density of $D_2O$ is approximately 1.107 gm/mL at 25 C. Accordingly, in some embodiments of the invention, the aqueous component includes 0-99% $D_2O$, or even higher. In some embodiments, the amount of $D_2O$ is in the range, for example without limitation, 10-99, 20-99, 30-99, 40-99, 50-99, 10-90, 20-90, 30-90, 40-90, 50-90%, and the like. In some embodiments, the content of $D_2O$ is a specific value, for example without limitation, about 1, 2, 5, 10, 20, 30, 40, 50, 60, 70, 80, 90, 95, 96, 97, 98, 99, or even 100% $D_2O$. In some embodiments, the first solution is substantially $D_2O$. The term "essentially $D_2O$" refers to $D_2O$ comprising the aqueous component with no additionally added $H_2O$. The terms "substantially $D_2O$" and like terms refer to $D_2O$ content in a range greater than 50%, for example without limitation, 55%, 60%, 65%, 70%, 75%, 80%, 85%, 90%, 95%, 99% or even 100% $D_2O$.

Figure 2:
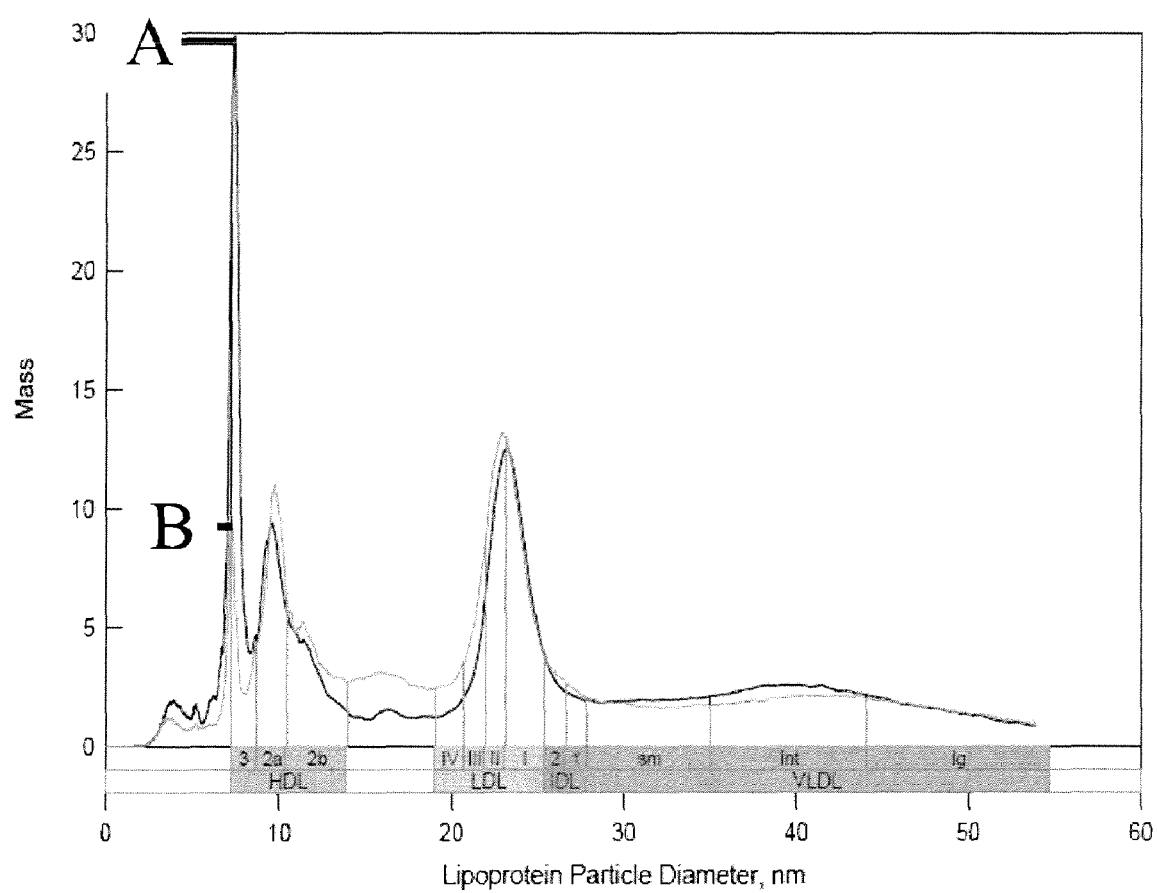
FIG. 2 shows a comparison of lipoprotein recovery from plasma using either a $D_2O$ or a low salt protocol (without $D_2O$) in a centrifugation separation experiment. Dark profile reflects a 2 hr centrifugation using $D_2O$ as the dense solution (1.107 g/mL). Light profile reflects a 3.7 hr centrifugation using KBr as the dense solution (1.151 g/mL). A—indicates peak height of albumin for 2 hr centrifugation; B—indicates the albumin peak height for 3.7 hr centrifugation. The abscissa is lipoprotein diameter (nm), and the ordinate is an arbitrarily scaled mass coordinate, as discussed in the legend for FIG. 1.

In some embodiments of this aspect, the lipoprotein-containing sample includes little if any added salt. With reference to FIG. 2 (experimental conditions provided in Example 1), which shows the result of a centrifgation procedure conducted using $D_2O$ and no additional salts for density adjustment, and a low-density salt solution without $D_2O$, approximately equivalent recovery of LDL and certain HDL fractions (e.g., HDL-IIb and HDL-IIa) was observed after 2 hrs ($D_2O$) and 3.7 hrs (low-density salt solution). With further reference to FIG. 2, the profiles for $D_2O$ and low-density salt centrifugation procedures result in similar profiles, with nonetheless increased albumin (peak at start of HDL 3 region) judged due to decreased centrifugation time with the $D_2O$ sample. Without wishing to be bound by any theory, it appears that reduction of salt content with concomitant increase in density using $D_2O$ results in shorter time required for centrifugation and purification of lipoprotein from a lipoprotein-containing sample.

Figure 3:
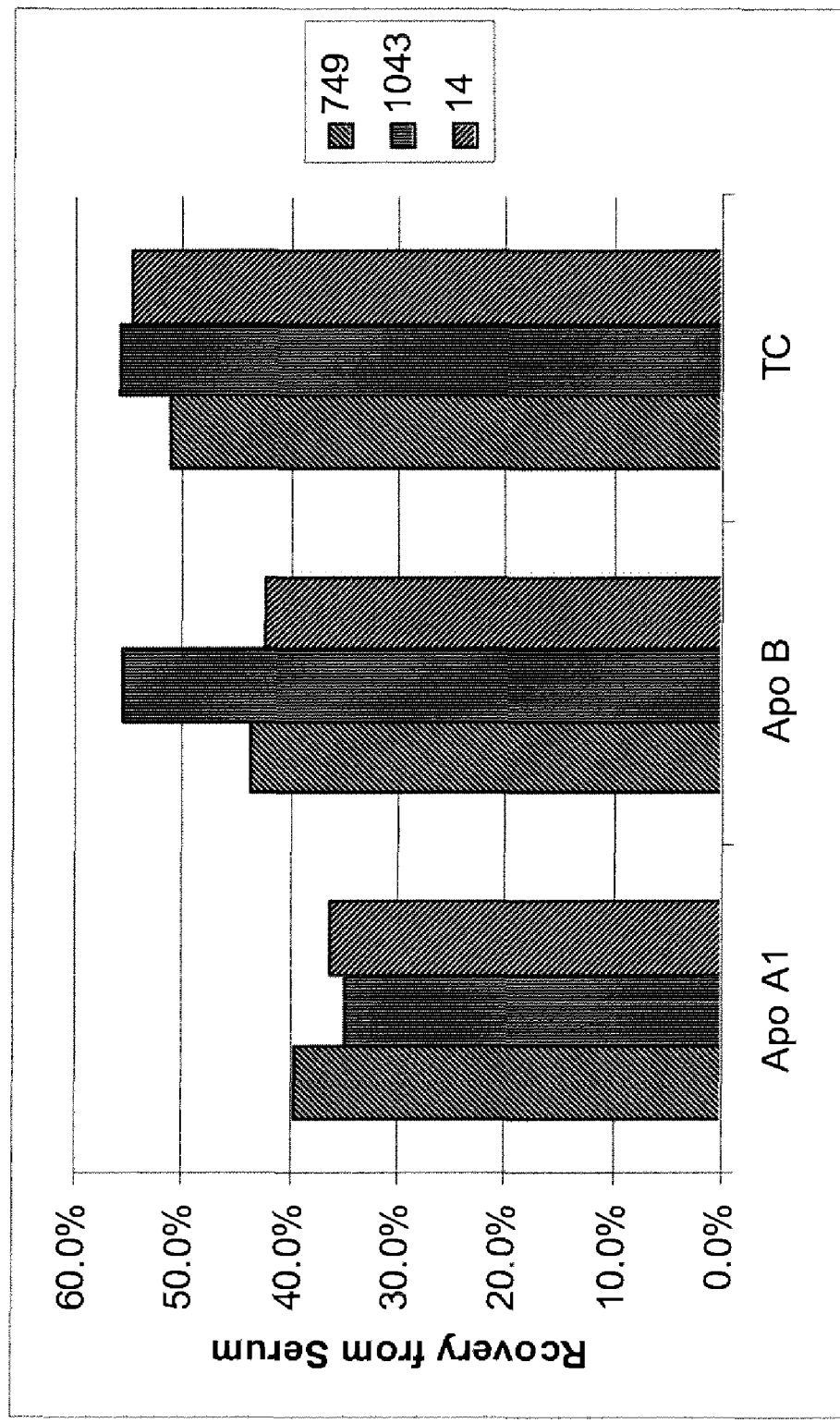
FIG. 3 shows the result of Apo A1, Apo B and total cholesterol (TC) recovery from plasma using $D_2O$ in combination with RGD/DS [RGD: Reactive Green 19 (RG 19) conjugated with dextran; RGD/DS: RGD in combination with DS] in a centrifugation separation experiment. Abscissa indicates analyte measured. Numbers associated with each box refer to a unique patient identification numbering system.

With reference to FIG. 3, under the conditions employed for FIG. 3 (experimental conditions of Example 2) approximately equal recovery of Apo A1 and Apo B after centrifugation are observed, indicating that lower density obtained with D$_2$O does not result in selective recovery of larger less dense particles.

In some embodiments of the method of the present invention directed to purifying lipoproteins by the placement of a less dense solution above and adjacent to a lipoprotein-containing sample solution prior to centrifugation, a single density adjustment of the lipoprotein-containing solution is conducted using inorganic salts, preferably NaCl and/or NaBr. For example, over this sample in a centrifuge tube can be layered a second solution having density less than the density of the lipoprotein-containing sample solution. Alternatively, the lipoprotein-containing sample solution can be introduced under the second solution in the centrifuge tube. The lipoprotein-containing sample density adjustment can be selected within the range of 1.00 to about 1.21 g/mL according to the densities in Table 1 to separate a class of lipoproteins having equal or lesser density. The density of the second solution can be selected within the range 1.00 g/mL up to just less than the density of the lipoprotein-containing sample solution, preferably in the range 1.00 to about 1.15 g/mL, more preferably 1.00 g/mL. In this manner, the HDL, IDL, LDL, Lp(a) and VLDL lipoproteins having densities less than the density of the lipoprotein-containing sample solution can be simultaneously extracted. Surprisingly, it has been found that providing a lipoprotein-containing solution in a centrifuge tube with a solution having lower density above and adjacent the lipoprotein-containing solution results in enhanced recovery of lipoprotein employing centrifugal separation. In preferred embodiments, lipoprotein containing fractions are withdrawn from the very top of the tube, at the meniscus, downward to the appropriate desired volume.

Further to these methods, it has been found that the time required for centrifugal separation of a lipoprotein-containing sample is reduced in lower density samples when compared to a corresponding period of time required for higher density samples. The terms "corresponding period of time" and the like in the context of centrifugal separation refer to the length of time of centrifugation required to achieve a specified level of separation, given equivalent centrifugal force during the centrifugation. For example without limitation, it has been found that at least 2 hrs centrifugation (at e.g., 230,000×G) is required to remove sufficient albumin from a typical lipoprotein-containing sample, with less centrifugation time resulting in less removal of albumin. Without wishing to be bound by any theory, it appears that by lowering the density of the sample, albumin, and indeed other non-lipoprotein plasma proteins, are more readily stratified and thus separated from lipoprotein. Accordingly, a key factor in optimizing purification of lipoprotein is shortening the time of centrifugation to maximize the loss of albumin and other plasma proteins while retaining HDL.

In some embodiments of aspects provided herein which contemplate centrifugation of sample containing lipoproteins and non-lipoprotein components, the sample further comprises a compound which can act as a precipitant for selected lipoprotein components therein, as known in the art. "Precipitant" refers to a compound which may cause or promote precipitation of a biomolecule upon addition to a solution of such biomolecule. A precipitant may require an additional agent to afford precipitation. "Additional agent to afford precipitation" and like terms refer to compounds which act with a precipitant and may be required to afford precipitation by the precipitant. Exemplary precipitants include, without limitation, salts of charged inorganic ions, preferably ammonium sulfate, antibodies, charged polymers (e.g., DS and the like) optionally in the presence of ionic species (e.g., divalent cations), lectins, and the like. In some embodiments, the precipitant is present albeit under conditions (e.g., pH, concentration, lack of necessary additional agents, and the like) wherein lipoproteins are not precipitated. In some embodiments, the precipitant is DS. In some embodiments, the precipitant is DS, and the necessary additional agent is a divalent cation. In some embodiments, the lipoprotein-containing sample comprises DS but lacks divalent cations. Without wishing to be bound by any theory, it is believed that DS binds to particles which contain lipids in the presence of divalent cations, and that DS binding may interfere with non-specific binding interactions with resulting enhancement of recovery of certain lipoproteins. For example without limitation, it is observed that inclusion of DS significantly improved recovery of LDL from some preparations described herein.

In some embodiments of aspects provided herein which contemplate centrifugation of sample containing lipoproteins and non-lipoprotein components, the sample further comprises an albumin-binding compound under conditions suitable to allow formation of a complex comprising albumin and albumin-binding compound Representative albumin-binding compounds include, without limitation, aromatic albumin-binding dyes. The aromatic albumin-binding dye may comprise a diazo dye; an alkali metal salt, alkaline earth metal salt, or amine salt of said diazo dye; a sulfonic acid dye; a physiologically-acceptable alkali metal salt, alkaline earth metal salt, or amine salt of said sulfonic acid dye; or mixtures thereof. Aromatic albumin-binding dyes particularly useful in the present invention include Reactive Blue 2, Evans Blue, Trypan Blue, Bromcresol Green, Bromcresol Purple, Methyl Orange, Procion red HE 3B, and the like. In certain embodiments, the albumin-binding compound is an analog of nicotinamide adenine dinucleotide (NAD). Representative NAD analogs suitable for use as albumin-binding compounds include, without limitation, RG 19, and Cibacrom Blue 3GA (CB 3GA).

In embodiments of the method contemplating the use of albumin-binding compounds, after mixture of the albumin-binding compound with a lipoprotein-containing sample, the sample is centrifuged as described herein. In some embodiments, the albumin-binding compound is conjugated with a chromatographic medium, which conjugate promotes facile removal of albumin complexed with albumin-binding compound for example, without limitation, by filtration. In some embodiments, the conjugated albumin-binding compound is observed to stratify at the bottom of the centrifuge tube, thereby facilitating removal (e.g., by aspiration, etc.) of the lipoprotein-containing fraction. In some embodiments wherein the albumin-binding compound is conjugated with a chromatographic medium, the chromatographic medium may be paramagnetic particles, dextran, agarose or Sephadex®, preferably dextran "Paramagnetic particle" as known in the art refers to particles having a magnetite core coated with a ligand, for example without limitation, streptavidin. The affinity of biotin for streptavidin ($K_d=10^{-15}$ M) is one of the strongest and most stable interactions in biology. Thus, paramagnetic particles combine convenient magnetic separation technology with the versatility and high affinity of the interactions such as the biotin-streptavidin interaction. It is observed that dextran conjugated albumin-binding compounds tend to remain soluble longer than other conjugate chromatographic media described herein. Without wishing to be bound by any theory, it is believed that the longer an albumin-binding compound can interact with albumin in a lipoprotein-containing sample, the more albumin-containing complex will be formed, thereby increasing purity and recovery of lipoprotein.

In further embodiments of the method contemplating the use of albumin-binding compounds, the albumin-binding compound is present during centrifugation at a concentration of up to 50 mg/mL, or even higher, without significant change in the quantity and relative proportion of the lipoproteins recovered from a plasma sample. For example, referring to FIG. 4, ion mobility analyses of a lipoprotein-containing sample in which varying amounts of RG 19 were included prior to centrifugation show that inclusion of RG 19 conjugated with dextran (RGD) results in recovery of lipoprotein with little, if any, effect on the distribution of lipoproteins; compare FIG. 1 with FIG. 4. With reference to Example 3 and FIG. 4, while the ion mobility profiles of HDL and LDL are similar, there is a decrease in the size of the peak (albumin) at the onset of the HDL 3 peak with increasing RGD concentration. Furthermore, the height of the peak at the higher concentrations is similar to that seen in preparations from lower density salt and 3.7 hr spins. In other embodiments, the concentration of albumin-binding compound is for example, without limitation, 1, 2, 5, 10, 15, 20, 25, 30, 35, 40, 45 or even 50 mg/mL.

Figure 5:
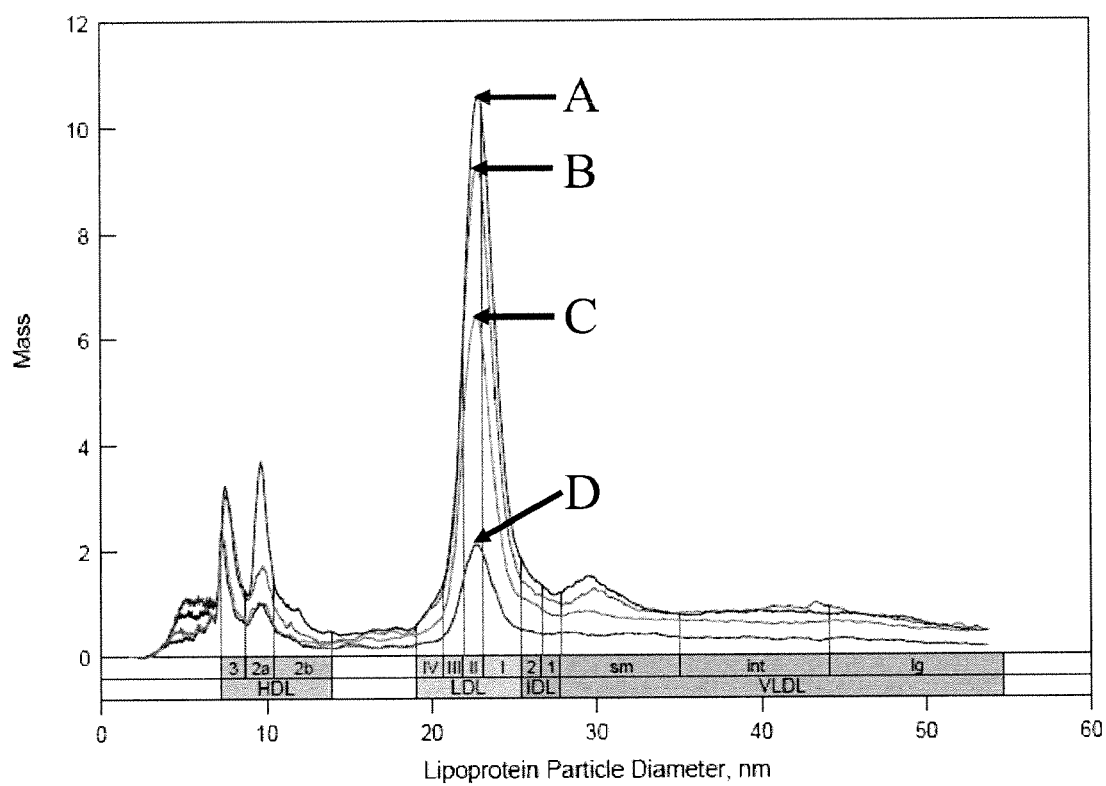
FIG. 5 shows the result of lipoprotein recovery from plasma after centrifugal purification with RGD and ethylenediaminetetracidic acid (EDTA), or with RGD/DS and EDTA, optionally ammonium acetate (AA). Legend: (B) extraction with 7.5 mg/mL RGD and 2.5 mg/mL DS, dilution with 25 mM ammonium acetate; (A) extraction with 7.5 mg/mL RGD and 2.5 mg/mL DS, dilution with 25 mM ammonium acetate with 5 ug/mL DS; (D) extraction with 7.5 mg/mL RGD, dilution with 25 mM ammonium acetate; (C) extraction with 7.5 mg/mL RGD, dilution with 25 mM ammonium acetate with 5 ug/mL DS. The abscissa is lipoprotein diameter (nm), and the ordinate is an arbitrarily scaled mass coordinate, as discussed in the legend for FIG. 1.

In certain embodiments, the invention provides for the use of an albumin-binding compound in combination with DS. Referring to FIG. 5, use of RGD, optionally DS, optionally ammonium acetate (AA), resulted in modulation of the recovery of LDL and HDL fractions as judged by ion mobility analysis. With reference to Example 4 and FIG. 5, there are similarities in the HDL region of the profiles shown in FIG. 5 with increased recovery of HDL when DS is present in the extraction (see "7.5/2.5" vs "7.5" legend entries in FIG. 5). Additionally, low albumin peak height is observed. It is believed that the increased peak in one preparation in HDL 2a (FIG. 5) is not typical of the reproducibility. Also of significance is the increased recovery of LDL. Without wishing to be bound by any theory, results herein suggest that DS present in the extraction and diluent affords the best recovery and reproducibility.

In certain embodiments, purified lipoprotein-containing sample obtained by methods of the invention are further diluted prior to ion mobility analysis. Referring to FIG. 6 and Example 5, the effect of presence or absense of DS (+/−5 ug/mL) in a 1:200 dilution step with 25 mM ammonium acetate prior to ion mobility analysis was assessed. As shown in FIG. 6, there is a significant increase in the LDL peak height in the presence of DS, whereas HDL peak profile are relatively unaffected.

In certain aspects and embodiments, the invention contemplates methods employing an albumin-binding compound conjugated with chromatographic media in combination with DS, and further in combination with a $D_2O$ solution under and adjacent a lipoprotein-containing sample in a centrifuge tube. A typical procedure employing this protocol is provided in Example 6.

In some embodiments of aspects provided herein which contemplate centrifugation of sample containing lipoproteins and non-lipoprotein components, the sample further comprises a non-lipoprotein capture ligand capable of binding non-lipoprotein component to form a non-lipoprotein/non-lipoprotein capture ligand complex, further wherein the centrifugation causes the non-lipoprotein/non-lipoprotein capture ligand complex to be separated from the lipoprotein components. "Non-lipoprotein capture ligand" and like terms refer to compounds which bind plasma components which are not lipoproteins. Exemplary non-lipoprotein capture ligands include, without limitation, antibodies and aptamers as understood in the art. For example without limitation, separation of antibody (i.e., as non-lipoprotein capture ligand) from antigen (i.e., non-lipoprotein) can be realized with a variety of methods including modulation of temperature, pH, salt concentration and the like. For further example without limitation, separation of aptamer (i.e., as non-lipoprotein capture ligand) from aptamer target (i.e., non-lipoprotein) can be realized with a variety of methods including modulation of temperature, pH, salt concentration, DNase or RNase and the like.

In some embodiments of aspects provided herein which contemplate centrifugation of sample containing lipoproteins and non-lipoprotein components, the sample further comprises a lipoprotein-capture ligand capable of binding lipoprotein component to form a lipoprotein/lipoprotein-capture ligand complex, further wherein the centrifugation causes the lipoprotein/lipoprotein-capture ligand complex to be separated from the non-lipoprotein components. "Lipoprotein-capture ligand" and like terms refer to compounds which bind lipoproteins. Exemplary lipoprotein-capture ligands include, without limitation, antibodies and aptamers as understood in the art. In preferred embodiments, the lipoprotein-capture ligand is an antibody.

In some embodiments of aspects provided herein which do not contemplate centrifugation of sample containing lipoproteins and non-lipoprotein components, the method contemplates a lipoprotein-capture ligand capable of binding lipoprotein component to form a lipoprotein/lipoprotein-capture ligand complex.

The term "aptamer" refers to macromolecules composed of nucleic acid, such as RNA or DNA, that bind tightly to a specific molecular target. The terms "bind," "binding" and the like refer to an interaction or complexation resulting in a complex sufficiently stable so as to permit separation. In some embodiments, the aptamer specifically bind Apo A1, Apo B, or Apo(a). Methods for the production and screening of aptamers useful for the present invention are well known in the art; see e.g., Griffin et al., U.S. Pat. No. 5,756,291, incorporated herein by reference in its entirety and for all purposes.

As practiced in the art, the method of selection (i.e., training) of aptamer requires a pool of single stranded random DNA oligomers comprising both random sequences and flanking regions of known sequence to serve as primer binding sites for subsequent polymerase chain reaction (PCR) amplification. Such DNA oligomers are generated using conventional synthetic methods well known in the art. As an initial and optional step, PCR amplification is conducted by conventional methods, and the amplified pool is left as duplex DNA, or used as single stranded DNA after strand separation. Optionally, transcription into RNA can be conducted. The term "oligomer pool" in this context refers to such single stranded or duplex DNA, or RNA transcribed therefrom. The term "refined oligomer pool" refers to an oligomer pool which has been subjected to at least one round of selection as described herein.

Further the aforementioned aptamer training, a "selection" step is conducted employing a column or other support matrix (i.e., target-coupled support) having target molecule attached thereon. Attachment, well known in the art, may be by covalent or non-covalent means. The oligomer pool, or refined oligomer pool, and target-coupled support are incubated in order to permit formation of oligonucleotide-target complex, and the uncomplexed fraction of the oligomer pool or refined oligomer pool is removed from the support environment by, for example, washing by methods well known in the art. Subsequent removal of oligonucleotide by methods well known in the art results in a refined oligomer pool fraction having enhanced specificity for target relative to a predecessor oligomer pool or refined oligomer pool.

Alternatively, the aforementioned aptamer training can employ a "reverse selection" step wherein aptamer is selected to bind to other constituents of the biological sample. In this case, a column or other support matrix is employed (i.e., constituent-coupled support) having other constituents of the biological sample attached thereon. The oligomer pool, or refined oligomer pool, and constituent-coupled support are incubated in order to permit formation of oligonucleotide-constituent complex, and the uncomplexed fraction of the oligomer pool or refined oligomer pool is removed from the support environment by, for example, washing by methods well known in the art. Subsequent removal of oligonucleotide by methods well known in the art results in a refined oligomer pool fraction having enhanced specificity for other constituents of the biological sample relative to a predecessor oligomer pool or refined oligomer pool. Examples of other constituents of the biological sample used in the reverse selection step include, without limitation, immunoglobulins and albumins.

In a typical production training scheme, oligonucleotide recovered after complexation with target or other constituent of the biological sample is subjected to PCR amplification. The selection/amplification steps are then repeated, typically three to six times, in order to provide refined oligomer pools with enhanced binding and specificity to target or other constituent of the biological sample. Amplified sequences so obtained can be cloned and sequenced. Optionally, when a plurality of individual aptamer sequence specific for a target having been obtained and sequenced, pairwise and multiple alignment examination, well known in the art, can result in the elucidation of "consensus sequences" wherein a nucleotide sequence or region of optionally contiguous nucleotides are identified, the presence of which correlates with aptamer binding to target. When a consensus sequence is identified, oligonucleotides that contain the consensus sequence may be made by conventional synthetic or recombinant means.

The term "antibody" refers to an immunoglobulin which binds antigen (e.g., lipoprotein or other component of the sample) with high affinity and high specificity. In this context "high affinity" refers to a dissociation constant of, for example without limitation, 1 µM, 100 nM, 10 nM, 1 nM, 100 pM, or even more affine, characterizing the binding reaction of antibody with antigen to which the antibody has been raised. The term "raised" refers to the production of high affinity antibody by methods long known in the art. Further in this context, the term "high specificity" refers to a preference of binding of a target antigen by a test antibody relative to non-target antigen characterized by a ratio of dissociation constants of, for example without limitation, 1, 2, 5, 10, 20, 50, 100, 200, 500, 1000, 10000, or more, in favor of binding of the target antigen to which the test antibody has been raised.

Methods of derivatization of antibodies and aptamers contemplated by the present invention include, for example without limitation, biotinylation. In some embodiments, the antibody or aptamer is biotinylated such that subsequent isolation on an avidin conjugated matrix, for example without limitation, an avidin chromatography column, affords facile separation by methods well known in the art of biochemical purification. In some embodiments, the biotinylated antibody or aptamer in complex with a lipoprotein is further subjected to streptavidin-conjugated magnetic beads. The ternary lipoprotein-biotinylated affinity reagent-streptavidin conjugated magnetic bead complex is then isolated by immunomagnetic methods well known in the art.

In some embodiments of this aspect, the lipoprotein-capture ligand is linked to a solid support by use of appropriate linkers well known in the art. Exemplary solid supports include, without limitation, paramagnetic particles, beads, gel matrix material (e.g., agarose, Sephadex®), and the like.

Further to this aspect, in some embodiments the present invention provides methods for removing Lp(a) from the sample prior to centrifugation, which method includes the following steps: (a) forming a precipitate of Lp(a) by admixing the sample with a precipitant for Apo B-containing lipoproteins under conditions sufficient to cause precipitation of Lp(a); and (b) isolating the Lp(a) containing precipitate from the first solution. "Preciptant for Apo B-containing lipoproteins" and like terms refer to compounds known to precipitate Apo B, as well known in the art.

In some embodiments of the present invention contemplating purification of lipoproteins collected by centrifugation methods provided herein, the present invention provides methods for removing Lp(a) from collected lipoproteins, which methods include the following steps: (a) forming a precipitate of Lp(a) by admixing the collected lipoproteins with a precipitant for Apo B-containing lipoproteins under conditions sufficient to cause precipitation of Lp(a); and (b) isolating the Lp(a) containing precipitate from the collected lipoproteins.

Further to methods provided herein for removing Lp(a) from a solution containing lipoprotein, an exemplary precipitant for Apo B is, without limitation, DS in the presence of divalent cation. In some embodiments, the divalent cation is $Mg^{2+}$. It has been observed that inclusion of DS results in a significantly enhanced recovery of LDL with little effect on recovery of HDL. DS can be mixed with lipoprotein-containing sample at a concentration in the range of about 0.1 to 50 mg/mL. In some embodiments, the DS concentration is about 0.1, 0.2, 0.5, 1.0, 1.5, 2.0, 2.5, 3.0, 4.0, 5.0, 10.0, 15.0, 20.0, 25.0, 30.0, 40.0 or even 50.0 mg/mL.

In further embodiments, the invention provides methods for obtaining purified Lp(a), which methods include the following steps: (a) solubilizing the Lp(a) containing precipitate obtained according to any of the methods provided herein therefor; (b) admixing the solubilized Lp(a) with a solid-support reagent containing a lectin attached to a solid support under conditions suitable to allow formation of a Lp(a)-lectin complex; (c) isolating the Lp(a)-lectin complex; and (d) releasing the Lp(a) from the Lp(a)-lectin complex, thereby providing purified lipoproteins suitable for example for ion mobility analysis.

Further to this method, the lectin may be selected from the group consisting of wheat germ agglutinin (WGA), lima bean agglutinin (LGA), phytohemaglutinin (PHA), and horseshoe crab lectin (HCL). In some embodiments, the lectin is WGA, In some embodiments, the solid support includes agarose. Methods of manipulation of such lectins, including reacting with Lp(a) to form a complex, isolating such a complex, and attaching lectin to a solid support, are well known in the art.

Further to this method, in some embodiments the releasing step includes washing the Lp(a)-lectin complex with a competitive ligand for the lectin. In some embodiments, the competitive ligand is N-acetylglucosamine (NAG). In some embodiments, the releasing step includes disulfide reduction, using a dilsufide reducing agent as known in the art, to reduce the disulfide linking apo (a) and Apo B, thereby releasing LDL.

In some embodiments of the present invention contemplating further purification of lipoproteins collected by centrifugation methods provided herein, the present invention provides methods for removing Lp(a) from collected lipoproteins, which methods include the following steps: (a) solubilizing the Lp(a) containing precipitate obtained according to any of the methods provided herein therefor; (b) admixing the solubilized Lp(a) with gamma globulins and proline; (c) precipitating the admixture by addition of a precipitant; and (d) recovering Lp(a) from the precipitate, thereby providing purified lipoproteins suitable for ion mobility analysis. As known in the art, "gamma globulin" refers to the γ-class of immunoglobulins. Exemplary precipitants include, without limitation, salts of highly charged inorganic ions, preferably ammonium sulfate. The concentration of gamma globulins useful for the present embodiment can be in the range 0.01-0.1 ug/mL, 0.1-1.0 ug/mL, 1.0-2.0-ug/mL, 2.0-5.0 ug/mL, 5.0-10.0 ug/mL, 10.0-100 ug/mL, 100-1000 ug/mL, or even higher. The concentration of proline can be in the range 10 uM-100 uM, 100-100-uM, 1-2 mM, 2-5 mM, 5-10 mM, or even higher.

Further to methods provided herein contemplating collected lipoprotein, in some embodiments the lipoprotein-containing solution is in contact with an inert centrifugation matrix. "Inert centrifugation matrix" and like terms in the context of centrifugal purification methods of the present invention refer to materials which do not chemically react with lipoproteins but which nonetheless enhance purification. Without wishing to be bound by any theory, it is believed that the inert centrifugation matrix acts to stabilize the contents of a centrifugation tube after centrifugation such that, for example, artifacts introduced during deceleration and/or pipetting of lipoprotein or other fraction from the tube are minimized. Exemplary inert centrifugation matrices include, without limitation, gel slurries or inert beads. In some embodiments, the gel slurry is a Sephadex® gel matrix. In some embodiments, the inert centrifugation matrix includes inert beads. Exemplary inert beads include, without limitation, glass beads, polystyrene beads, and the like, adapted to sink to the bottom of the first solution in a centrifuge tube. Inert beads can be of any convenient size, for example without limitation, about 0.1, 0.2, 0.5, 0.6, 0.7, 0.8, 0.9, 1.0, 1.1, 1.2 1.3, 1.4, 1.5, 1.6, 1.7, 1.8, 2.0, 2.2, 2.4, 2.6, 2.8, 3.0, 3.3, 3.6, 3.9, 4.0 mm, or even smaller or larger.

In some embodiments of the aspect of the present invention directed to methods for purifying lipoproteins for ion mobility analysis by the use of polyanionic compounds and one or more divalent cations, the polyanionic compound is selected from the group consisting of DS, amylopectin and polyvinyl sulfate, preferably DS. In some embodiments, the divalent cation is selected from the group consisting of $Mg^{2+}$ and $Ca^{2+}$, preferably $Mg^{2+}$.

In some embodiments, the present invention provides methods for purifying lipoproteins for ion mobility analysis, which methods do not include centrifugation. In some embodiments, a solution comprising lipoproteins and non-lipoproteins is admixed with one or more lipoprotein-capture ligands capable of binding lipoproteins to form a lipoprotein/lipoprotein-capture ligand complex. In some embodiments, after formation of a lipoprotein/lipoprotein-capture ligand complex, the complex so formed is isolated by methods known in the art including, without limitation, immunomagnetic methods. In some embodiments, after isolation of a lipoprotein/lipoprotein-capture ligand complex, the liprotein is released from the lipoprotein/lipoprotein-capture ligand complex by methods known in the art and described herein.

In view of any of the aspects contemplating isolation and/or purifying of lipoproteins described herein, in another aspect the invention provides methods for analyzing the size distribution of lipoproteins by ion mobility analysis. In some embodiments, the one or more lipoproteins are obtained from a body fluid such as a plasma specimen from an individual. In some embodiments, the one ore more lipoproteins are selected from the group consisting of HDL, LDL, Lp(a), IDL and VLDL. In some embodiments, the method further includes the step of using the determined lipoprotein size distribution to conduct an assessment of the individual, the assessment selected from the group consisting of lipid-related health risk, cardiovascular condition, risk of cardiovascular disease, and responsiveness to a therapeutic intervention.

"Assessment" in the context of lipid-related health risk, cardiovascular condition, and risk of cardiovascular disease, refers to a statistical correlation of the resulting lipoprotein size distribution with population mortality and risk factors, as well known in the art. Assessment in the context of responsiveness to a therapeutic intervention refers to comparison of the lipoprotein size distribution before and after a therapeutic intervention is conducted. Exemplary therapeutic interventions include, without limitation, the administration of drugs to an individual for the purpose of lowering serum cholesterol, lowering LDL, IDL, and VLDL, Lp(a) and/or raising HDL, as known in the art.

In some embodiments, the results of lipoprotein analyses are reported in an analysis report. "Analysis report" refers in the context of lipoprotein and other lipid analyses contemplated by the invention to a report provided, for example to a clinician, other health care provider, epidemiologist, and the like, which report includes the results of analysis of a biological specimen, for example a plasma specimen, from an individual. Analysis reports can be presented in printed or electronic form, or in any form convenient for analysis, review and/or archiving of the data therein, as known in the art. An analysis report may include identifying information about the individual subject of the report, including without limitation name, address, gender, identification information (e.g., social security number, insurance numbers), and the like. An analysis report may include biochemical characterization of the lipids in the sample, for example without limitation triglycerides, total cholesterol, LDL cholesterol, and/or HDL cholesterol, and the like, as known in the art and/or described herein An analysis report may further include characterization of lipoproteins, and references ranges therefore, conducted on samples prepared by the methods provided herein. The term "reference range" and like terms refer to concentrations of components of biological samples known in the art to reflect typical normal observed ranges in a population of individuals. Exemplary characterization of lipoproteins in an analysis report may include the concentrations of non-HDL lipoproteins and Lp(a) determined by ion mobility. Further exemplary characterization of lipoproteins, determined for example by ion mobility analyses conducted on samples prepared by methods of the invention, include the concentration and reference range for VLDL, IDL, Lp(a), LDL and HDL, and subclasses thereof. An analysis report may further include lipoprotein size distribution, obtaining for example by ion mobility analysis, of a sample prepared by methods of the invention. Entries included in an exemplary analysis report are provided in Example 7.

EXAMPLES

Example 1

Comparison of Lipoprotein Purification Using $D_2O$ and Low-salt Solution

A serum sample (25 uL) was processed either using a low-density salt solution (1.151 g/mL) (i.e., "low-density salt sample") or $D_2O$ (200 uL each). Samples were centrifuged at 223,000×G for 3.7 hr (low-density salt sample) or 2 hr ($D_2O$).

Following removal of the top 100 uL after centrifugation, the low-density salt sample was dialyzed against ammonium acetate solution and diluted to 1:200 before ion mobility analysis. The $D_2O$ sample was diluted directly after centrifugation to 1:200 with ammonium acetate prior to ion mobility analysis. Results of ion mobility analysis are presented in FIG. 2.

Example 2

Effect of Purification on Apo A, Apo B, and TC Recovery

To assess whether HDL (Apo A1) was preferentially lost in procedures employing $D_2O$, three samples as shown in FIG. 3 (i.e., 749, 1043, 14: arbitrary and unique patient identification numbers) were subjected to lipoprotein isolation employing $D_2O$ together with RGD/DS solution (7.5/2.5 mg/mL, respectively) to remove albumin. Samples were each prepared in replicates of six. The isolated individual top 100 uL were each analyzed for content of Apo A1 (HDL), Apo B (LDL, IDL, VLDL) and total cholesterol (TC). Plasma or serum apolipoproteins AI and B were measured by standardized ELISA using commercially available monoclonal capture antibodies (Biodesign International, Saco, Minn.) and anti-human goat polyclonal detection antibodies, purified and biotinylated, (International Immunology Corp., Murrieta, Calif.) in a non-competitive sandwich-style immunoassay. Concentration was measured by addition of streptavidin conjugated peroxidase followed by color development using ortho-phenyline-diamine. Lipoprotein calibrators were standardized using CDC #1883 serum reference material (Center for Disease Control, Atlanta, Ga.) and pooled reference sera (Northwest Lipid Research Clinic, Seattle, Wash.). Total cholesterol was measured using commercially available assay kit reagents (Bayer Health Care, Tarrytown, N.Y.) according to manufacturers instructions and modified for analysis of 25 µl serum or plasma plus 200 µl cholesterol reagent per microtiter plate well. Standards, controls, samples and reagent background were measured after color development using a microtiter plate reader. The results (FIG. 3) show the mean recovery of each sample compared to the total present in each serum. Without wishing to be bound by any theory, the purification procedure did not result in preferential loss of HDL, as judged by equivalent recovery of Apo A1 and Apo B.

Example 3

Effect of Varying RGD on Lipoprotein Fraction Recovery

Figure 4:
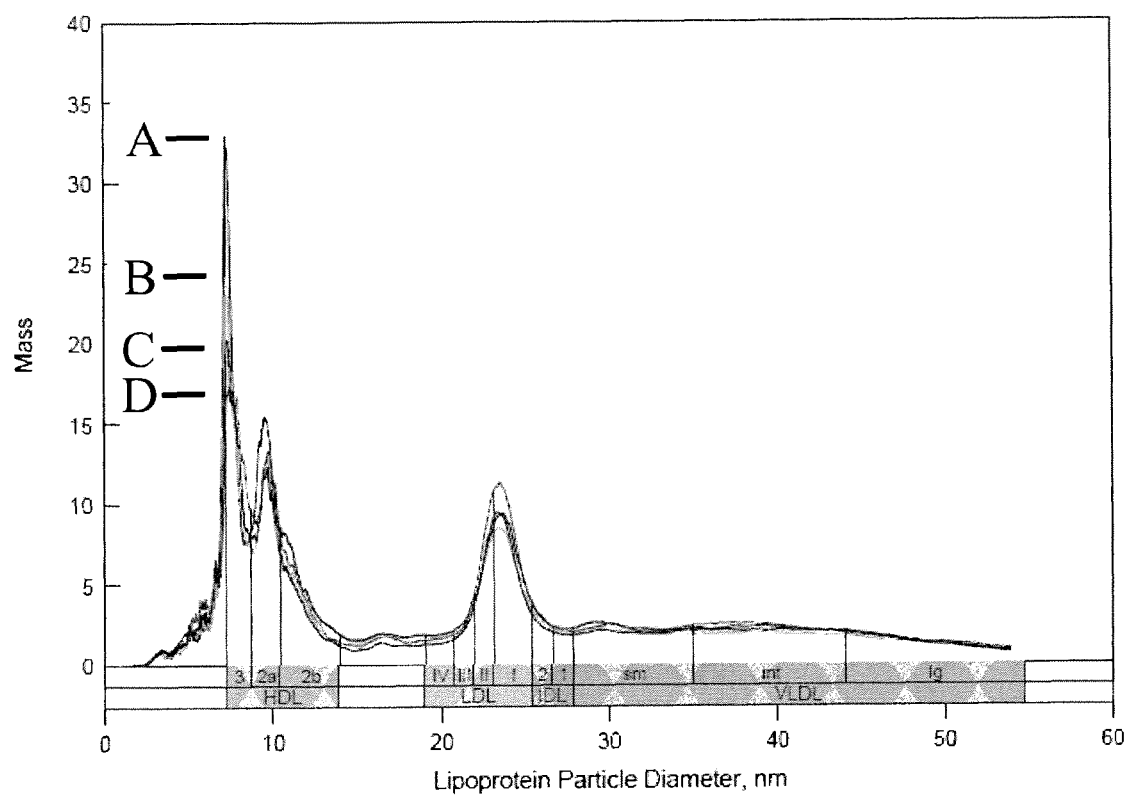
FIG. 4 shows the result of lipoprotein recovery from plasma after centrifugal purification using RGD. RGD was added to samples at various concentrations and centrifuged for 2 hr 15 min using $D_2O$ as the dense solution. Albumin Peak heights are indicated for the four different concentrations of RGD used; A, 10 mg/mL RGD; B, 15 mg/mL RGD; C, 20 mg/mL RGD; and D, 25 mg/mL RGD. The abscissa is lipoprotein diameter (nm), and the ordinate is an arbitrarily scaled mass coordinate, as discussed in the legend for FIG. 1.

A serum sample was mixed with varying amounts of RGD (10, 15, 20, 25 mg/mL) and incubated on ice for 15 min before being overlaid on a cushion of $D_2O$. After centrifuging for 120 min at 223,000×G, the top 100 uL was removed and diluted 1:200 with ammonium acetate solution. Samples were then analyzed by ion mobility analysis. Results are shown in FIG. 4.

Example 4

Purification of Lipoproteins Employing RG 19, DS, AA

With reference to FIG. 5, in order to assess the effect of DS on the removal of albumin and recovery of lipoproteins in both the extraction/purification and diluent, a serum sample (5 uL) was extracted with 20 uL of 7.5 mg/mL RGD alone (legend "C/D" in FIG. 5) or 20 uL of a combination of 7.5 mg/mL RGD and 2.5 mg/mL DS (legend "A/B" in FIG. 5). The DS molecular weight used for both the extraction and diluent is 10K. After 15 min incubation on ice each sample was centrifuged for 2 hr 15 min at 223,000×G at 10 C. The top 100 uL was removed and diluted 1:200 with either 25 mM ammonium acetate solution (legend "B/D" in FIG. 5) or 25 mM ammonium acetate containing 5 ug/mL DS (legend "A/C" in FIG. 5).

Example 5

Result of Purification of Lipoproteins Employing DS in Diluent

With reference to FIG. 6, a lipoprotein-containing serum sample prepared by a 18 hr density separation, using methods well known in the art, was employed after dialysis to assess the effect of DS in the diluent on the recovery of LDL. An aliquot of the centrifuged serum sample was diluted 1:200 with 25 mM ammonium acetate in the absence of DS and subjected to ion mobility analysis. Another aliquot was diluted 1:200 with 25 mM ammonium acetate in the presence of 5 ug/mL DS. Duplicate runs of each sample are shown in FIG. 6.

Example 6

Purification of Lipoproteins Employing RG 19, DS, $D_2O$

Lipoprotein-containing samples obtained from plasma were mixed briefly by vortexing. Five uL of sample, or optionally control, were mixed with 20 uL of an albumin removal reagent containing 7.5 mg/mL RGD (Sigma), 2.5 mg/mL DS (Sigma) and 0.5 mg/mL EDTA (Spectrum Chemicals) and incubated on ice for 15 min. Following incubation the sample mixture was overlaid on $D_2O$ (Medical Isotopes) 200 uL in a Ti 42.2 ultracentrifuge tube (Beckmann). The samples were then ultracentrifuged at 10° C. for 135 min at 223,000×g (42,000 rpm). Following ultracentrifugation the lipid fraction (85 µL) was removed from the top of the centrifuge tube. Prior to analysis by ion mobility, the samples were diluted to a final dilution of 1:800 in 25 mM ammonium acetate 0.5 mM ammonium hydroxide pH 7.4 for HDL analysis. For LDL analysis samples were diluted 1:200 in the same diluent containing 5 ug/mL DS. Final dilutions were made in deep well 96 well plates and placed in an autosampler with the cool stack maintained at 6° C., prior to ion mobility analysis.

Example 7

Result of Purification and Analysis of Lipoproteins in Serum Samples

Serum was separated from whole blood collected via venipuncture. Following separation the serum was divided into three portions, one aliquot analyzed for HDL, triglycerides, and total cholesterol content using traditional methods well known in the art. LDL is calculated from these results. In preferred embodiments, if triglycerides are greater than 400 mg/dL then LDL is measured directly. The second aliquot was analyzed for its Lp(a) content using an immunoassay, well known in the art. Ion mobility analysis was employed for the third aliquot to fractionate the lipoproteins.

In a typical production procedure, sample(s) together with controls, one sample known to be LDL pattern A (control A) and one sample known to be pattern B (control B) as known in the art, are placed on the Perkin Elmer JANUS multiprobe. 30 uL of controls and sample(s) are transferred to a separate tube and mixed, and 120 uL of the RG19 dextran, DS, EDTA solution is added. The tubes are then transferred to ice for a 15-minute incubation. Following the 15 min incubation the tubes are returned to the multiprobe. In the meantime, centrifuge tubes have had two 4 mm beads added to them, and these are then placed on the multiprobe where 120 uL of $D_2O$ is added to each centrifuge tube. Controls and sample(s) are then overlaid on the $D_2O$ by the multiprobe before being transferred to the ultracentrifuge rotor (Ti 42.2). Samples are then spun for 135 min at 10 C at 223,000×G (42,000 rpm). Following centrifugation, the centrifuge tubes are removed carefully and placed on the multiprobe where the top 85 uL (+/−5 uL) is removed to a separate tube. Once all samples are collected the multiprobe makes two dilutions for each control and sample. One dilution is a final dilution of 1:200 with ammonium acetate solution containing 5 ug/mL DS; the second is a 1:800 dilution with just ammonium acetate solution. The two dilutions are then run on the ion mobility instrument. Following analysis the particle numbers are converted to nmol/L using conversions well known in the art. The data from the HDL run (1:800) and the larger lipoproteins (1:200) are combined and reported together with the biochemical data from aliquots 1 and 2. The profile of the lipoproteins is also reported as well as the total LDL particle concentration and the LDL peak particle size, which is used to determine the LDL phenotype. An exemplary assessment report resulting from combining these data is provided in Table 2 (numerical representation) and FIG. 7 (graphical representation of lipoprotein profile).

TABLE 2

Lipoprotein Fraction by Ion Mobility

| Assay Component | In Range | Out of Range | Units | Reference Range |
|---|---|---|---|---|
| Lipid Panel | | | | |
| Cholesterol, Total |  | 328 (High)* | mg/dL | <200 |
| LDL Cholesterol |  | 249 (High) | mg/dL | <130 |
| HDL Cholesterol | 62 |  | mg/dL | >50 |
| VLDL Cholesterol | 17 |  | mg/dL | <30 |
| Triglycerides | 85 |  | mg/dL | <150 |
| Non-HDL Cholesterol |  | 266 (High) | mg/dL | <160 |
| Lipoprotein (a) | 25 |  | nmol/L | <75 |
| LDL Particle Profile | | | | |
| LDL Particles, Total | 886 |  | nmol/L | 272-1181 |
| LDL Particle size | 228.1 |  | Ang | 215.4-232.9 |
| LDL Phenotype | A |  | Type** | A |
| Lipoprotein Particles | | | | |
| LDL I large |  | 226 (High) | nmol/L | 51-186 |
| LDL II large | 426 |  | nmol/L | 91-574 |

TABLE 2-continued

Lipoprotein Fraction by Ion Mobility

| Assay Component | In Range | Out of Range | Units | Reference Range |
|---|---|---|---|---|
| LDL III small | 187 |  | nmol/L | 82-442 |
| LDL IV small | 47 |  | nmol/L | 33-129 |
| HDL 2b large | 1425 |  | nmol/L | 384-1616 |
| HDL 2a intermediate |  | 5616 (High) | nmol/L | 903-3779 |
| HDL 3 small |  | 9229 (High) | nmol/L | 475-4244 |
| IDL 1 large |  | 39 (High) | nmol/L | 10-38 |
| IDL 2 small |  | 66 (High) | nmol/L | 11-48 |
| VLDL large |  | 1.9 (High) | nmol/L | 0.2-1.8 |
| VLDL intermediate |  | 6.4 (High) | nmol/L | 1.0-5.7 |
| VLDL small | 25.1 |  | nmol/L | 5.8-26.6 |

*"High" and "Low" refer to above or below range, respectively.
**"Type" refer to phenotype as determined by particle size with cutoff approximately at LDL II (215.4 A), as known in the art.

To obtain more accurate lipoprotein profile using differential ion mobility as discussed above, one may adjust the results for any loss of lipoprotein during handling (e.g. sample centrifugation, pipeting and dilutions) prior to the ion mobility apparatus. This may be achieved by adding one more types of labeled lipoproteins to a sample as an internal standard. By following the label during processing, the recovery of the labeled lipoprotein can be used to adjust upwards the concentration of the same but unlabeled lipoprotein present in the original sample. For example, an aliquot of the lipoprotein isolate after centrifugation is measured for fluorescent signal and compared with an aliquot directly from the starting stock sample (not centrifuged). The difference in signal represents the proportion of unknown sample recovered, and allows a more accurate calculation of lipoprotein concentration in plasma or serum.

The following method was used to conjugate a fluorescent molecule to HDL subfractions. This method may be applied to other types of lipoproteins. HDL was isolated from plasma by sequential flotation to obtain lipoproteins within density interval 1.063-1.20 g/mL. The total HDL fraction was then dialyzed to salt background density 1.184 g/mL and centrifuged for 28 hrs at 40,000 rpm, 10° C. in a fixed angle 50.3 Beckman rotor. The 6 ml centrifuge tube was then pipetted to obtain predominantly large, intermediate and small HDL subfractions, T[0-1], T[1-3] and T[3-6], respectively. The subfractions were then dialyzed against 100 mM NaHCO3, pH 8.5, 4° C. overnight. Protein concentration was measured in each subfraction using the Lowry method.

HDL subfractions were then labeled with fluorescent probe AlexaFluor 488 (carboxylic acid, succinimidyl ester 'mixed isomers', Molecular Probes Cat # A-20000, Mol. Wt. 643.42, Abs @494 nm/Em 517 nm) according to manufacturer's instructions. Briefly, HDL subfractions were combined with AF488 at a suggested optimal ratio 10:1 (wt:wt) maintaining optimal concentrations of HDL and AF488, >2 mg/ml and 10 mg/ml, respectively. The protocol and quantities of the solutions used are listed below.

| Incubation Mixtures: | | | | | | | | |
|---|---|---|---|---|---|---|---|---|
| | Stk Ligand | | | Stk AF488 | | | Tot. Vol | Stop Soln |
| | Co | | | Co | | | | |
| HDL Subfr. | mg/ml | μl | mg | mg/ml | μl | mg | μl | μl |
| T[0-1] | 3.59 | 560 | 2.01 | 10 | 20.104 | 0.2010 | 580 | 40 |
| T[1-3] | 3.18 | 625 | 1.99 | 10 | 19.875 | 0.1988 | 645 | 40 |

-continued

| | Incubation Mixtures: | | | | | | | |
|---|---|---|---|---|---|---|---|---|
| | Stk Ligand Co | | | Stk AF488 Co | | | Tot. Vol | Stop Soln |
| HDL Subfr. | mg/ml | µl | mg | mg/ml | µl | mg | µl | µl |
| T[3-6] | 6.39 | 785 | 5.02 | 10 | 50.162 | 0.5016 | 835 | 100 |
| | | | | Total | 90.1405 | 0.901405 | | |

1-Add HDL subfr to glass vial with mag-stir bar
2-While stirring at rm. temp., add AF488 volume to ligand slowly.
3-Incubate mixture for 1 hour w/ continuous stirring.
4-Add Stop Soln (1.5 M Tris, pH 8.0). Incubate at rm temp 30 min.
5-Dialyze labeled HDL Subfrs to 20 mM Tris. 150 mM NaCl, 0.27 mM EDTA, pH8 [in cold box, protect from light] vs. 1 liter overnite, and 2 × 1 L dialysate volume changes.

The AF488 labeled HDL subfractions were then tested for signal sensitivity at various dilutions in buffer from 250 to >30000. The labeled HDL subfractions were also tested for signal sensitivity when diluted in various plasma preparations before and after centrifugation for isolation of lipoproteins.

Additional dilution and sensitivity tests were performed after a second centrifugal isolation of the labeled HDL subfractions at density <1.23 g/mL to remove unconjugated fluorescent label from the HDL:AF488 conjugates.

The fluorescent probe fluorescein-5-EX, succinimidyl ester, obtained from Molecular Probes (Cat # F-6130), was used to label HDL subfractions in the same manner as described above for AF488. The above methods were also used to fluoresencently label VLDL and LDL. Additional tests were conducted to fluoresence label combined high molecular weight standards (Pharmacia HMW Standard Mix) containing thyroglobulin, apoferritin, catalase, lactate dehydrogenase, and albumin.

In embodiments of aspects of the present invention contemplating analysis and/or display of lipoprotein distributions, as exemplified without limitation by FIG. 1, FIG. 7 and the like, the ion mobility data, obtained with a differential ion mobility analyzer, can be processed prior to presentation for clinical interpretation. Unless otherwise specified, "differential ion mobility data" and like terms in the context of raw data from an ion mobility analysis, or processed data for presentation for clinical interpretation, refer to differential ion mobility particle size distributions having an independent variable correlated to the diameter of a particle, and an observed dependent variable correlated with particle count. In some embodiments, the independent variable is voltage or the corresponding electrical field generated by the voltage (see Eqn. 3). In some embodiments, the independent variable is particle diameter. In some embodiments, the dependent variable is particle count. In some embodiments, the dependent variable is the number of particles counted during a specified time period, for example without limitation 0.001-0.01, 0.01-0.1, 0.1-1, 1-2 s or even longer. In some embodiments, the specified time period is 0.1 s.

"Processing of the differential ion mobility data" and like terms refer to manipulations of data, which manipulations, when taken in total, may provide graphical and/or numeric results which accurately and reproducibly reflect the lipoprotein distribution, and/or concentrations of individual lipoprotein classes and subclasses thereof, within a sample. Exemplary manipulations useful in the processing of differential ion mobility particle size distribution data include, without limitation, multiplication by a constant, convolution with a function, addition and/or subtraction of a constant numeric value or a function including without limitation correction for the contribution of a contaminant, numeric integration, smoothing, and other arithmetic manipulations known in the art. Accordingly, processing of the differential ion mobility particle size distribution data can be employed for a variety of reasons, including without limitation, correction to accurately reflect physiological concentrations of lipoproteins in a sample, scaling to correct for specific instrument and process efficiencies, removal of data representing contributions of a contaminant, and the like. "Specific instrument and process efficiencies" and like terms refer to the detection and correction for changes in analyte (e.g., lipoprotein) concentration during processing and analysis. Exemplary specific instrument efficiencies include an apparent dilution introduced during electrospray wherein formation of the Taylor cone results in an apparent dilution of lipoprotein in the resulting particle-laden gas stream. Efficiencies are measured by methods employing instruments having quantified efficiencies well known to practitioners in the art. "Contribution of a contaminant" and like terms in the context of differential ion mobility particle size distribution data refer to data, for example without limitation particle count from a differential ion mobility instrument analysis, resulting from non-lipoprotein species counted in the differential ion mobility instrument and included in the differential ion mobility particle size distribution data obtained therefrom. Exemplary non-lipoprotein species in this context include, without limitation, any reagent disclosed herein and albumin in monomeric and/or multimeric form.

In some embodiments, the contribution to the ion mobility particle size distribution data due to a reagent described herein is subtracted from the ion mobility size distribution data during processing of the data. For example, without wishing to be bound by any theory, it is believed that a contribution due to RGD in particle size distribution data from a differential ion mobility analysis (i.e., differential ion mobility particle size distribution data having particle count versus particle diameter) can be represented by a one or more decaying exponential functions over selected diameter regions. Accordingly, in some embodiments the differential ion mobility particle size distribution data are fit in a selected region to a function having the form of Eqn 4:

$$y_1 = k_1 * e^{(-0.7*d)} \quad (4)$$

wherein $y_1$ is the best fit for the contribution to the ion mobility as determined by methods well known in the art, $k_1$ is an empirical constant of the fit, and d is the particle diameter. The above Eqn. 4 is valid for particle diameters of greater than 2 nm. In some embodiments, the region of the fit is 3-6, 3-4, 3-5, 3-6, 4-6, or 5-6 nm (particle diameter), preferably 3-4 nm. In some embodiments, the entire set of ion mobility data is corrected by the function resulting from a fit to Eqn. 4.

In some embodiments, the differential ion mobility particle size distribution data are further processed to account for a contribution due to albumin inclusion in the sample taken for ion mobility analysis. In some embodiments, the construction of a correction for albumin (i.e. "albumin correction curve") is initially afforded by a piecewise function having the following form:

| Region | Dependent variable region, nm | Functional correction |
|---|---|---|
| 1 | 0 <= d < 7 | 0 |
| 2 | 7 <= d < 7.1 | $y_2 = k_2 * e^{(-2.56*7.1)}$ Eqn. (5) |
| 3 | 7.1 <= d < 8.5 | $y_3 = k_3 * e^{(-2.56*d)}$ Eqn. (6) |
| 4 | 8.5 <= d < 15 | Empirical (from spiked albumin data) | wherein $y_2$ and $y_3$ are the functional values in regions 2 and 3, respectively, $k_2$ and $k_3$ are empirical constants determined by methods well known in the art, and d is the particle diameter. "Empirical (from spiked albumin data)" refers to the effect on ion mobility particle size distribution data of subtracting from the distribution an amount of albumin equivalent to the amount of albumin in the measured distribution.

In some embodiments, the albumin correction curve is further modified to account for the presence of albumin dimer. It has been found empirically that albumin dimer is typically present in samples for ion mobility analysis in the range 1-10%, 1-8%, 2-8%, 2-7%, 2-6%, 2-5%, preferably 2%, and that an albumin correction curve can be scaled in a particular region to account for, and to gradually suppress, the presence of albumin dimer. In some embodiments, the lower diameter limit of this particular region is 0, 1, 2, 3, 4, 5, 6, 7, 8, 9, 10, 11 or even 12 nm. In some embodiments, the upper diameter limit of this particular region is 1, 2, 3, 4, 5, 6, 7, 8, 9, 10, 11, 12, 13, 14 or even 15 nm. In some embodiments, the range of this particular region is 0-15, 5-10, 7-9, preferably 7.9-8.4 nm. Accordingly, the albumin correction curve can be modified by a function having the form of Eqn 7:

$$y' = y * ((d - \text{lowerlimit}) * 2 * \text{dimer} + (\text{upperlimit} - d) * 2) \quad (7)$$

wherein y is the albumin correction curve, y' is the albumin correction curve after gradual suppression of the presence of albumin dimer, d is the particle diameter, lowerlimit and upperlimit are the lower and upper size limits for the correction, respectively, and dimer is the selected percentage dimer concentration. In some embodiments, the region in which the presence of dimer is suppressed is between 7.9 nm (lowerlimit) and 8.4 nm (upperlimit).

In some embodiments, a theoretical curve representing albumin monomer is fit to the ion mobility particle size distribution of a sample in a particular region, using curvefitting methods well known in the art. In some embodiments, this theoretical curve is represented by a function having the form of Eqn. 8:

$$y_m = k_m * e^{(-k_a * d)} \quad (8)$$

wherein $y_m$ is the theoretical number distribution of albumin monomer, $k_m$ and $k_a$ are empirically derived constants In some embodiments, $k_a$ is in the range 0.1-10, 1-5, 2-4 or 2-3. In some embodiments, $k_a$ is 2.56. In some embodiments, this particular region is the range 0-15, 5-10, 6-9, 7-8, preferably 7.3-7.5 nm. In some embodiments, after determination of the contribution of albumin monomer which results in the best fit to Eqn. 8, the ion mobility particle size distribution data are corrected by subtracting Eqn. 7 therefrom, scaled by the same contribution. In some embodiments, the correction afforded by subtracting Eqn. 7 is conducted in a particular region, for example without limitation, 0-15, 2-12, 4-10, preferably 6-10 nm. In some embodiments wherein the correction does not contemplate the range 10-11 nm, a corresponding correction in the region 10-11 nm is conducted by multiplying Eqn 7. by a factor of (11-diameter) and subtracting the result from the ion mobility particle size distribution data.

The process described above may be implemented in a variety of electronic devices, such as desktop or laptop computers or handheld devices, for example. Such devices are well known to those skilled in the art. Additionally, the results may be displayed on a monitor, printed or stored on a memory device, such as a hard drive, CD ROM, CD R/W, flash memory or the like. Further, the results may be made available to other devices through a network, which may be a private network or a public network, such as the Internet. In this regard, the electronic device and/or the memory device may be accessible through the network.

In one embodiment, the measured values are compared to empirically determined ranges to perform a diagnosis based on a patient's serum or plasma values falling within or outside a range The chart below illustrates one exemplary set of ranges for such a diagnosis:

| nmol/L | | HDL 3 | | HDL 2a | | | HDL 2b | |
|---|---|---|---|---|---|---|---|---|
| Female | 475 | — | 4224 | 903 | — | 3779 | 384 | — | 1616 |
| Male | 613 | — | 3344 | 1174 | — | 3744 | 169 | — | 1153 |

| nmol/L | LDL IV | | LDL III | | | LDL II | | LDL I | | | LDL Total | |
|---|---|---|---|---|---|---|---|---|---|---|---|---|
| Female | 33 | — | 129 | 82 | — | 442 | 91 | — | 574 | 51 | — | 186 | 272 | — | 1189 |
| Male | 38 | — | 164 | 136 | — | 627 | 200 | — | 596 | 48 | — | 164 | 508 | — | 1279 |

| | LDL Paricle Size (A) | |
|---|---|---|
| Female | 215.4 | — | 232.9 |
| Male | 212.3 | — | 230.9 |

| nmol/L | | IDL 2 | | | IDL 1 | |
|---|---|---|---|---|---|---|
| Female | 11 | — | 48 | 10 | — | 38 |
| Male | 12 | — | 59 | 11 | — | 41 |

-continued

| nmol/L | VLDL sm | | | VLDL int | | | VLDL lg | |
|---|---|---|---|---|---|---|---|---|
| Female | 5.8 | — | 26.6 | 1.0 | — | 5.7 | 0.2 | — | 1.8 |
| Male | 5.0 | — | 23.0 | 1.1 | — | 7.3 | 0.2 | — | 2.5 |

Ion mobility spectrometry provides a way to measure the size distribution of nanoparticles based on gas-phase particle electrical mobility. This methodology was adapted for measuring the size distribution of lipoprotein particles. The method was automated and generated profiles of particle number and particle mass versus particle diameter in about one minute. Lipoproteins are first enriched (plasma protein removal) by ultracentrifugation and then diluted in a volatile buffer and electrosprayed. A charge neutralization process leaves a well-characterized fraction of the particles with a single charge. The charged particles are drawn through a Differential Mobility Analyzer (DMA), which allows particles of a narrow size to pass to a particle counter as a function of a voltage applied to the DMA. By scanning the applied voltage, particle number distributions are obtained for HDL, LDL, IDL and VLDL. The measurements are based on first principles and do not need to be calibrated with respect to particle size. Particle number distributions are converted into particle mass distributions. Using this method, the intra-assay variation for LDL diameter was <0.6%, for concentration, <10% for HDL and LDL and <15% for IDL and VLDL. The inter-assay reproducibility was <1.0% for LDL particle size, and for concentration, <15% for HDL and LDL and <20% for IDL and <25% for VLDL. The table below shows the summary data, expressed as mean and SD, used to generate reference ranges for the individual lipoprotein fractions. A total of 259 healthy individuals (191 F, 68 M) who met the current NCEP ATP III criteria for optimal lipid/lipoprotein levels: total cholesterol (chol) <200, LDL chol <100, HDL chol >40 (M) >50 (F), triglyceride <150 mg/dL were used in the study. The results show the expected difference between genders, males having higher concentrations of smaller LDL particles and females having increased HDL 2b.

| Lipoprotein Fraction | Gender | Mean nmol/L | SD nmol/L | P males vs females |
|---|---|---|---|---|
| HDL 3 | Female | 1443 | 847 | 0.071 |
| | Male | 1646 | 602 | |
| HDL 2b | Female | 834 | 299 | <0.003 |
| | Male | 494 | 258 | |
| HDL 2a | Female | 2343 | 719 | 0.850 |
| | Male | 2325 | 655 | |
| LDL IV | Female | 70 | 24 | <0.003 |
| | Male | 84 | 31 | |
| LDL III | Female | 212 | 103 | <0.003 |
| | Male | 313 | 125 | |
| LDL II | Female | 336 | 125 | <0.003 |
| | Male | 407 | 119 | |
| LDL I | Female | 112 | 35 | 0.012 |
| | Male | 100 | 29 | |
| Total LDL | Female | 727 | 227 | <0.003 |
| | Male | 893 | 193 | |
| | | Angstrom | Angstrom | |
| LDL Peak Diameter | Female | 225.7 | 4.48 | <0.003 |
| | Male | 221.7 | 4.19 | |
| IDL 1 | Female | 16 | 9 | 0.003 |
| | Male | 20 | 11 | |
| IDL 2 | Female | 25 | 10 | 0.007 |
| | Male | 29 | 12 | |
| VLDL small | Female | 11.2 | 5.7 | 0.506 |
| | Male | 10.7 | 4.8 | |
| VLDL inter | Female | 3.0 | 1.3 | <0.003 |
| | Male | 3.7 | 1.6 | |
| VLDL large | Female | 0.9 | 0.4 | <0.003 |
| | Male | 1.2 | 0.6 | |

Ranges for the remainder of the population (abnormal) with one or more criterion outside the ATP III guidelines were determined. These showed expected differences with increased concentrations of smaller LDL as well as decreased size and decreased concentration of HDL 2b (B) with little change in HDL 2a and 3.

The methods described above may be carried out in a variety of apparatuses. For example, U.S. Patent Publication No. 2003/0136680 to Benner et al. describes an apparatus by which a sample solution in a centrifuging tube is expelled through a capillary tube where it becomes ionized by the electrospray process as it exits the capillary tube. Thus, the pressure differential caused by the pressure chamber transfers the ionized sample into a gas stream, which then carries the sample to a mobility analyzer. Once the sample in the centrifuging tube is analyzed, another tube of sample is placed within the pressure chamber. In this arrangement, however, since only a small volume of the sample is provided at any time in a centrifuging tube, the flow rate of the sample through the capillary can vary substantially over time even if the pressure in the pressure chamber is maintained, thereby affecting the quantitative determinations from the ion mobility analyzer based on predicted flow rates.

Embodiments of the present invention address these concerns. In accordance with embodiments of the invention, a constant flow rate is achieved by pumping the sample through a capillary and by ionizing (or charging) the sample within the capillary during flow to the ion mobility analyzer. FIG. 8 illustrates an exemplary apparatus for ion mobility analysis according to an embodiment of the invention. The ion mobility analysis apparatus 10 of FIG. 8 includes an ion mobility analyzer 20 similar to that illustrated in U.S. Patent Publication No. 2003/0136680. The ion mobility analyzer 20 is capable of counting particles flowing therethrough. The ion mobility analyzer 20 may be provided with an electronic device (not shown), such as a computer, capable of processing the data in accordance with, for example, the algorithm described above.

A charged particle stream of the sample is provided to the ion mobility analyzer 20 from an autosampler 22. The autosampler 22 may be a robotic system for automatically supplying a sample. One such autosampler is model HTC PAL, Leap Technologies of Carrboro, N.C. In one embodiment, the autosampler is a robotic device that only supplies purified sample from a rack of tubes or from a multiwell plate to the pump(s). The autosampler 22 can provide a substantially continuous supply of samples for ion mobility analysis without the need for substantial human intervention.

Sample from the autosampler 22 is supplied to a first pump 26 through an injection port 24. In this regard, the autosampler 22 may include a reservoir (not shown) in which the purified sample is contained. The injection port 24 may be a part of the first pump 26. The first pump 26 is a high flow-rate (or high-flow) pump capable of pumping the sample from the autosampler 22 at a relatively high flow rate (e.g., greater than or equal to 1.0 microliter per minute). In one embodiment, the high-flow pump pumps the sample from the autosampler 22 at a rate of approximately 5-20 microliters per minute. Most preferably, the high-flow pump pumps the sample at a rate of approximately 10 microliters per minute. Suitable high flow pumps are obtained from Eksigent Technologies, 2021 Las Positas Ct Suite 161, Livermore, Calif.

From the first pump 26, the sample is supplied to a second pump 30. The second pump 30 is a low flow-rate (or nanoflow) pump capable of pumping the sample to a capillary 34 at a relatively low rate (e.g., less than or equal to 1.0 microliters per minute) to enable proper ionization or charging of the particles of the sample, as described below. In one embodiment, the nanoflow pump pumps the sample to the capillary at a rate of approximately 100-200 nanoliters per minute. Most preferably, the nanoflow pump pumps the sample at a rate of approximately 200 nanoliters per minute. Suitable nanoflow pumps are obtained from Eksigent Technologies, 2021 Las Positas Ct Suite 161, Livermore, Calif.

In one embodiment, a combination pump assembly may be used in place of the two pumps. For example, a pump assembly may include a high-flow component and one or more nanoflow components. An exemplary combination pump assembly is NanoLC 1-D, available from Eksigent Technologies, 2021 Las Positas Ct Suite 161, Livermore, Calif.

In one embodiment, the first pump 26 may supply the sample to a plurality of nanoflow pumps through either a single valve 28 or a plurality of valves.

Flow to and through the capillary 34 may be controlled via a valve 32, which may be part of the second pump 30 or may be a separate valve positioned within the capillary 34. The valve 32 ensures a constant flow rate of the sample through the capillary 34 downstream of the valve 32. The valve 32 may be electronically controlled to maintain the constant flow rate. In this regard, the valve may be controlled in response to sensors or meters positioned downstream of the valve 32.

The sample particles are charged during their flow through the capillary 34 by an ionizer 40. As will be understood by those skilled in the art, the actual ionization or charging of the particles may occur as the particles exit the capillary into the ion mobility analyzer. In one embodiment, the ionizer 40 is a conductive union assembly positioned around a portion of the capillary 34. Conductive unions (also known as a conductive junctions) apply an electrical current around a very thin flow to provide an electrical charge to the flow. One exemplary conductive union assembly is described in U.S. Pat. No. 7,075,066, which is incorporated herein by reference in its entirety. The charged sample particles are then supplied through the capillary 34 to the ion mobility analyzer 20.

FIGS. 9A and 9B illustrate exemplary embodiments of the conductive union for use in charging the flow of the sample particles through the capillary. Referring first to FIG. 9A, a conductive union assembly 40*a* is formed around the capillary 34. An ionization region 35 of the capillary 34 is surrounded by a conductive union 42. A voltage applied to the conductive union 42 causes charging of the particles in the flow through the ionization region 35 of the capillary 34. For a detailed explanation of the operation of the conductive union assembly 40*a*, reference may be made to U.S. Pat. No. 7,075,066.

Referring now to FIG. 9B, another embodiment of a conductive union assembly is illustrated. In the embodiment of FIG. 9B, a conductive union assembly 40*b* forms a microtite region 37 in a portion of the capillary 34 through which the sample flows. The microtite region 37 may form a joint, or a seal, between two sections of the capillary. The microtite region 37 has a small dead volume in which the sample particles are charged. In one embodiment, the microtite region 37 has a dead volume of approximately 5-50 nanoliters. In a most preferred embodiment, the microtite region 37 has a dead volume of approximately 10-15 nanoliters. The microtite region 37 is preferably formed of stainless steel. The conductive union assembly 40*b* includes a conductive union 44 formed around the microtite region 37. A voltage applied to the conductive union 44 causes charging of the particles in the flow through the microtite region 37.

Thus, the ion mobility analyzer 20 is provided with a controlled nanoflow of the sample at a substantially time-invariant rate. In this regard, the flow rate preferably varies by less than five percent from a nominal rate, more preferably by less than two percent and, most preferably by less than one percent. This allows for a more consistent and reliable analysis to be performed by the ion mobility analyzer 20.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses which will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention.

Thus, additional embodiments are within the scope of the invention and within the following claims.

What is claimed is:

1. A method for purifying lipoproteins suitable for differential charged-particle mobility analysis of lipoprotein class and subclass, said method comprising:
   (a) preparing a centrifuge tube containing a first solution underneath a sample and a second solution above said sample, said sample comprising high density lipoproteins (HDL) and non-lipoprotein components, said first solution having a first density greater than 1.00 g/mL and less than or equal to about 1.21 g/mL, and said second solution having a second density greater than or equal to 1.00 g/mL and less than said first density;
   (b) subjecting said tube to centrifugation sufficient to cause said non-lipoprotein components to migrate toward the bottom of the tube and away from said lipoproteins, thereby providing purified lipoproteins;
   wherein said sample further comprises dextran sulfate under conditions wherein said HDL are not precipitated from said sample.

2. The method according to claim 1, wherein said first density is in the range of about 1.15 g/mL to about 1.21 g/mL.

3. The method according to claim 1, wherein said HDL and non-lipoprotein components are from a plasma sample.

4. The method according to claim 1, wherein said centrifugation does not reach equilibrium.

5. The method according to claim 1, further comprising:
   (c) collecting said purified lipoproteins from the top portion of said centrifuge tube following centrifugation.

6. The method according to claim 5, wherein Lp(a) is removed from said collected lipoproteins by:
   (a) forming a precipitate comprising Lp(a) by admixing said collected lipoproteins with a precipitant for Apo B-containing lipoprotein under conditions sufficient to cause precipitation of Lp(a); and
   (b) isolating said Lp(a) containing precipitate from the collected lipoproteins.

7. The method according to claim 1,
   wherein said sample further comprises an albumin-binding compound capable of binding albumin to form an albumin-albumin binding compound complex, and
   wherein said centrifugation causes said albumin-albumin binding compound complex to be separated from said purified lipoproteins.

8. The method according to claim 7, wherein said albumin-binding compound is an analog of nicotinamide adenine dinucleotide (NAD).

9. The method according to claim 8, wherein said NAD analog is selected from the group consisting of Reactive Green 19 and Cibacrom Blue 3GA.

10. The method according to claim 8, wherein said NAD analog is conjugated to a chromatographic medium selected from the group consisting of paramagnetic particles, dextran, and agarose.

11. The method according to claim 1,
    wherein said sample further comprises a non-lipoprotein capture ligand capable of binding non-lipoprotein to form a non-lipoprotein/non-lipoprotein capture ligand complex, and
    wherein said centrifugation causes said non-lipoprotein/non-lipoprotein capture ligand complex to be separated from said lipoprotein components.

12. The method according to claim 11,
    wherein said non-lipoprotein capture ligand is selected from the group consisting of aptamer and antibody.

13. The method according to claim 1, wherein Lp(a) is removed from said sample prior to centrifugation by:
    (a) forming a precipitate of Lp(a) by admixing said sample with a precipitant for Apo B-containing lipoprotein under conditions sufficient to cause precipitation of Lp(a); and
    (b) isolating said Lp(a) containing precipitate from said sample.

14. The method according to claim 13, wherein said precipitant for Apo B-containing lipoprotein comprises dextran sulfate and a divalent cation.

15. The method according to claim 14, wherein said divalent cation is $Mg^{2+}$.

16. The method according to claim 1, wherein said first solution comprises deuterium oxide.

17. The method according to claim 16, wherein said first solution comprises a solvent that is substantially deuterium oxide.

18. The method according to claim 1, wherein said first solution is in contact with an inert centrifugation matrix.

19. The method according to claim 18, wherein said inert centrifugation matrix comprises gel slurry or inert beads.

20. The method according to claim 19, wherein said gel slurry comprises a gel matrix.

21. The method according to claim 19, wherein said inert centrifugation matrix comprises inert beads.

22. The method according to claim 1, wherein said sample further comprises one or more lipoproteins selected from the group consisting of intermediate density lipoproteins (IDL), very low density lipoproteins (VLDL), and lipoprotein (a) (Lp(a)).

23. The method according to claim 22, wherein said sample further comprises low density lipoproteins (LDL).

24. The method according to claim 23, wherein said sample further comprises three or more of IDL, VLDL, Lp(a), and LDL.

25. A method for purifying lipoproteins, said method comprising:
    (a) preparing a centrifuge tube containing a sample and a first solution located below and adjacent to said sample, said sample comprising one or more lipoproteins and non-lipoprotein components,
       said sample further comprising Reactive Green dextran and dextran sulfate,
       said first solution comprising deuterium oxide; and
    (b) subjecting said tube to centrifugation sufficient to cause said non-lipoprotein components to migrate toward the bottom of the tube and away from said lipoproteins.

26. The method according to claim 25, wherein said first solution has a density in the range 1.00 g/mL to about 1.21 g/mL.

27. The method according to claim 25, wherein said first solution has a density in the range 1.00 g/mL to about 1.10 g/mL.

* * * * *

UNITED STATES PATENT AND TRADEMARK OFFICE
CERTIFICATE OF CORRECTION

PATENT NO. : 8,247,235 B2
APPLICATION NO. : 11/760672
DATED : August 21, 2012
INVENTOR(S) : Michael P. Caulfield et al.

It is certified that error appears in the above-identified patent and that said Letters Patent is hereby corrected as shown below:

IN THE SPECIFICATION

Column 4, line 26:

Change "121 g/mL" to --1.21 g/mL--.

Column 5, line 18:

Change the word "liporoteins" to --lipoproteins--.

Column 6, line 33:

Add a --,-- after "(nm)".

Column 9, line 14:

Change "$e=1.6.\times 0.10^{-19}$" to --$e=1.6 \times 10^{-19}$--.

Column 9, line 21:

Delete the "." after equation (3).

Column 18, line 11:

Change the word "Preciptant" to --Precipitant--.

Column 18, line 59:

Change the word "dilsufide" to --disulfide--.

Column 19, line 58:

Change the word "liprotein" to --lipoprotein--.

Signed and Sealed this
Twenty-sixth Day of February, 2013

Teresa Stanek Rea
*Acting Director of the United States Patent and Trademark Office*

Column 19, line 67:

Change the word "ore" to --or--.

Column 20, line 38:

Add a --.-- after the word "herein".

Column 23, line 14:

Add a --°-- after "10" and before "C" to read --10°C--.

Column 28, line 7 of the chart:

Change the word "Paricle" to --Particle--.

IN THE CLAIMS

Claim 5, Column 33, line 40:

Change "(c)" to --(a)--.